US012465716B2

(12) United States Patent
Nanda et al.

(10) Patent No.: US 12,465,716 B2
(45) Date of Patent: Nov. 11, 2025

(54) VENTILATOR

(71) Applicants: Sunil Nanda, Bangalore (IN); Pankaj Kumar Porwal, Udaipur (IN)

(72) Inventors: Sunil Nanda, Bangalore (IN); Pankaj Kumar Porwal, Udaipur (IN)

( * ) Notice: Subject to any disclaimer, the term of this patent is extended or adjusted under 35 U.S.C. 154(b) by 995 days.

(21) Appl. No.: 17/557,752

(22) Filed: Dec. 21, 2021

(65) Prior Publication Data

US 2023/0001126 A1 Jan. 5, 2023

(30) Foreign Application Priority Data

Jul. 1, 2021 (IN) ............................ 202141029551

(51) Int. Cl.
*A61M 16/20* (2006.01)
*A61M 16/00* (2006.01)

(52) U.S. Cl.
CPC ...... *A61M 16/204* (2014.02); *A61M 16/0003* (2014.02); *A61M 16/0078* (2013.01); *A61M 2016/0027* (2013.01); *A61M 2205/52* (2013.01); *A61M 2205/70* (2013.01)

(58) Field of Classification Search
CPC ............ A61M 16/204; A61M 16/0003; A61M 2016/0027; A61M 2205/52; A61M 2205/70; A61M 16/125; A61M 16/1045; A61M 16/0051; A61M 16/024; A61M 16/06; A61M 16/0672; A61M 16/1005; A61M 16/106; A61M 16/16; A61M 16/208; A61M 2210/0618; A61M 2202/0208; A61M 2205/18; A61M 2205/3368; A61M 2205/505; A61M 2230/46; A61M 16/0072–0084
See application file for complete search history.

(56) References Cited

U.S. PATENT DOCUMENTS

| | | | | |
|---|---|---|---|---|
| 11,007,344 | B2 * | 5/2021 | Sayani | A61M 16/0084 |
| 11,406,787 | B2 * | 8/2022 | Oldfield | A61M 16/204 |
| 11,744,969 | B2 * | 9/2023 | Nataraj | G01F 1/363<br>128/204.23 |
| 2007/0157931 | A1 * | 7/2007 | Parker | A61M 11/005<br>128/204.23 |
| 2009/0241952 | A1 * | 10/2009 | Nicolazzi | A61M 16/026<br>703/2 |
| 2019/0336713 | A1 * | 11/2019 | Piracha | A61M 16/0084 |

(Continued)

*Primary Examiner* — Elliot S Ruddie
(74) *Attorney, Agent, or Firm* — CHIP Law Group

(57) ABSTRACT

Provided is a ventilator that includes a breathing system, a mechanical system coupled to breathing system, and a control system coupled to breathing system and mechanical system. The control system includes pressure sensors, processing circuitry, and memory configured to store a look-up table. The processing circuitry receives a set of values for plurality of parameters, identifies a compression value from a plurality of compression values in the look-up table based on the received set of values. The processing circuitry causes the mechanical system to compress a bag valve of the breathing system in accordance with the identified compression value. The compression of the bag valve causes a gaseous inhalant to flow through the breathing system within a time-interval. The processing circuitry determines an actual volume of the gaseous inhalant and iteratively modifies the compression value of the bag valve to match a desired volume of the gaseous inhalant.

20 Claims, 10 Drawing Sheets

(56) References Cited

U.S. PATENT DOCUMENTS

2020/0086075 A1* 3/2020 Mujeeb-U-Rahaman .................. A61M 16/0003
2021/0205556 A1* 7/2021 Ahmadi Noorbakhsh ................. G06K 7/10366
2021/0330914 A1* 10/2021 Young ................ A61M 16/161

* cited by examiner

400

| | PEEP ($mmH_2O$) | Vt (ml) | RR (bpm) | IE Ratio | Compression Value | Integral Q |
|---|---|---|---|---|---|---|
| S1 | 30 | 250 | 10 | 1/2 | 444 | 43056 |
| S2 | 30 | 300 | 10 | 1/2 | 498 | 49231 |
| S3 | 50 | 300 | 15 | 1/2 | 505 | 43324 |
| S4 | 50 | 350 | 15 | 1/3 | 556 | 49028 |
| S5 | 100 | 450 | 20 | 1/3 | 708 | 55720 |

FIG. 4

VENTILATOR

CROSS-RELATED APPLICATIONS

This application claims priority of Indian Non-Provisional Application No. 202141029551, filed Jul. 1, 2021, the contents of which are incorporated herein by reference.

FIELD

Various embodiments of the disclosure relate generally to a ventilator. More specifically, various embodiments of the disclosure relate to methods and systems for controlling a ventilator.

BACKGROUND

In wake of an exponential rise in respiratory problems in individuals, due to multiple underlying issues (for example, coronavirus disease, pneumonia, asthma, snakebites, or the like), use of ventilators has become very crucial. Availability of a ventilator at the right time could prevent further deterioration of health of a patient. However, the healthcare sector often faces shortage of ventilators. A few reasons behind such shortage of the ventilators are its high cost of manufacturing and repair. The fact that ventilators are fragile and break down easily makes it even more difficult for the healthcare sector to maintain availability of a sufficient number of ventilators at all times.

A known reason behind such high cost of manufacturing and repair of ventilators is the use of expensive components in the ventilators. For example, a flow sensor used in a ventilator, to measure a tidal volume of air flowing via the ventilator, is a cost-intensive component. Further, the flow sensor tends to break down very easily and hence leads to a frequent requirement for maintenance of the ventilator, which adds to the cost of the ventilator. Such sudden break down of the ventilator may be fatal to an individual in its need, and hence may cause loss of lives and emotional trauma. Also, such components may be cost intensive to replace/repair and may also cause financial loss to an owner of the ventilator.

In light of the foregoing, there exists a need for a technical and reliable solution that overcomes the abovementioned problems and provides a robust and inexpensive ventilator.

Limitations and disadvantages of conventional and traditional approaches will become apparent to one of skill in the art, through comparison of described systems with some aspects of the present disclosure, as set forth in the remainder of the present application and with reference to the drawings.

SUMMARY

Ventilators, methods and systems for controlling ventilators are provided substantially as shown in, and described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

FIG. 4 is a table that illustrates an exemplary look-up table, in accordance with an exemplary embodiment of the disclosure;

DETAILED DESCRIPTION

Figure 1:
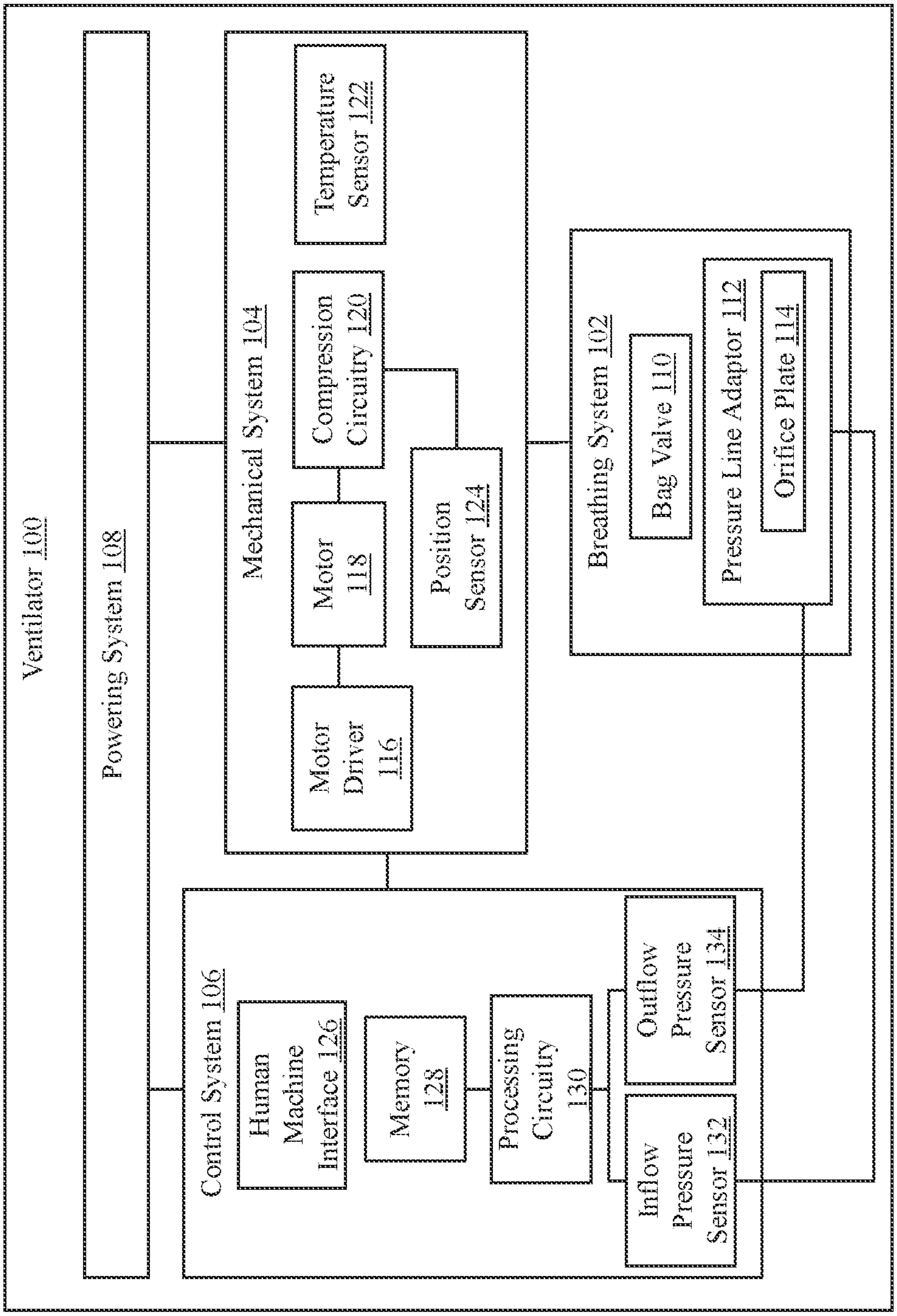
FIG. 1 is a block diagram that illustrates a ventilator, in accordance with an exemplary embodiment of the disclosure.

Certain embodiments of the disclosure may be found in the disclosed ventilator, systems, and methods for controlling ventilators. Exemplary aspects of the disclosure provide methods for controlling a ventilator. The methods include various operations that are executed by a control system to control a ventilator. In an embodiment, the ventilator includes a breathing system, a mechanical system coupled to the breathing system, and a control system coupled to the breathing system and the mechanical system. The breathing system includes a bag valve and the mechanical system is configured to compress the bag valve. The control system includes a plurality of pressure sensors, processing circuitry, and a memory configured to store a look-up table that includes a plurality of compression values corresponding to a plurality of values of a plurality of parameters. The control system is configured to receive a set of values for the plurality of parameters and identify a compression value from the plurality of compression values in the look-up table based on the received set of values. The control system is further configured to cause the mechanical system to compress the bag valve in accordance with the identified compression value to deliver a desired volume of a gaseous inhalant to a patient through the breathing system within a time-interval. The compression of the bag valve causes the gaseous inhalant to flow through the breathing system. The control system is further configured to determine an actual volume of the gaseous inhalant delivered to the patient based on pressure values recorded by the plurality of pressure sensors in response to the flow of the gaseous inhalant through the breathing system. The control system is further configured to iteratively modify the compression value of the bag valve based on a deviation of the actual volume of the gaseous inhalant from the desired volume of the gaseous inhalant. The compression value is iteratively modified until the actual volume of the gaseous inhalant delivered to the patient matches the desired volume of the gaseous inhalant.

In an embodiment, the plurality of parameters includes a respiration rate (RR) for a user, an inhalation-exhalation (IE) ratio for the user, a desired volume of the gaseous inhalant to be delivered to the user, and a positive end expiratory pressure (PEEP) to be maintained in lungs of the user.

In another embodiment, the breathing system further includes a pressure line adaptor having a front end that faces the bag valve and a rear end that faces the patient.

In another embodiment, the pressure line adaptor includes an orifice plate having an inflow face and an outflow face. The inflow face of the orifice plate allows an inflow of the gaseous inhalant via the orifice plate and the outflow face of the orifice plate allows an outflow of the gaseous inhalant from the orifice plate.

In another embodiment, the pressure line adaptor further includes a first pressure tap and a second pressure tap. The first pressure tap is positioned between the front end of the pressure line adaptor and the orifice plate and the second pressure tap is positioned between the orifice plate and the rear end of the pressure line adaptor.

In another embodiment, the plurality of pressure sensors includes an inflow pressure sensor and an outflow pressure sensor. The inflow pressure sensor is positioned at the first pressure tap and the outflow pressure sensor is positioned at the second pressure tap.

In another embodiment, the inflow pressure sensor is configured to record an inflow pressure due to the flow of the gaseous inhalant between the front end of the pressure line adaptor and the orifice plate, and the outflow pressure sensor is configured to record an outflow pressure due to the flow of the gaseous inhalant between the orifice plate and the rear end of the pressure line adaptor.

In another embodiment, the control system further includes a human machine interface configured to receive the set of values as an input setting for the plurality of parameters.

In another embodiment, the look-up table is generated during calibration of the ventilator. The ventilator is calibrated by correlating the plurality of compression values of the bag valve and the plurality of values of the plurality of parameters with a volume of the gaseous inhalant that flows through the breathing system.

In another embodiment, the control system is further configured to determine, based on the received set of values, the time-interval within which the bag valve is to be compressed in accordance with the identified compression value.

In another embodiment, the control system is further configured to identify the desired volume of the gaseous inhalant to be delivered to the patient from the look-up table based on the received set of values.

The methods and systems of the disclosure provide a solution for ensuring a robust and cost-effective ventilator. The ventilator provided herein is compact and modular. Hence, the ventilator is portable. The disclosed ventilator is configured to record a volume of gaseous inhalant being delivered to the patient without having a flow sensor therefor. Hence, the ventilator is free from breakdowns caused due to a damage of the flow sensor. The ventilator may be used in an uncontrolled environment and hence may also be deployed in ambulances. The disclosed ventilator increases accessibility to a ventilation facility and in turn, improves chances of survival of a patient.

FIG. 1 is a block diagram that illustrates a ventilator, in accordance with an exemplary embodiment of the disclosure. Referring to FIG. 1, shown is the ventilator 100 that includes a breathing system 102, a mechanical system 104, a control system 106, and a powering system 108. The control system 106 is coupled to the breathing system 102 and the mechanical system 104. The powering system 108 is coupled to the mechanical system 104 and the control system 106. The breathing system 102 includes a bag valve 110 and a pressure line adaptor 112 having an orifice plate 114. The mechanical system 104 includes a motor driver 116, a motor 118, compression circuitry 120, a temperature sensor 122, and a position sensor 124. The motor driver 116 is coupled to the motor 118 which in turn is coupled to the compression circuitry 120. The compression circuitry 120 is coupled to the position sensor 124. The control system 106 includes a human machine interface (HMI) 126, a memory 128, processing circuitry 130, an inflow pressure sensor 132, and an outflow pressure sensor 134. The processing circuitry 130 is coupled to the memory 128, the inflow pressure sensor 132, and the outflow pressure sensor 134. The inflow pressure sensor 132 and the outflow pressure sensor 134 are further coupled to the pressure line adaptor 112. It will be apparent to a person skilled in the art that the statement that two or more components are "coupled" together shall mean that the components are joined together either directly or joined through one or more intermediate parts.

The ventilator 100 is a mechanized device that supports or enables delivery of a gaseous inhalant into lungs of a patient who is failing or inadequate in maintaining a respiratory cycle (i.e., breathing cycle) on their own. The gaseous inhalant may be oxygen, blended air and oxygen, a drug diffused in air or oxygen, or the like that has to be delivered into the lungs of the patient. The ventilator 100 may operate in a plurality of modes such as continuous mandatory ventilation (CMV), synchronized assist control ventilation (Sync ACV), synchronized intermittent mandatory ventilation type 1 (SIMV1), and synchronized intermittent mandatory ventilation type 2 (SIMV2).

In each mode of operation, the ventilator 100 may provide one of pressure-controlled ventilation and volume-controlled ventilation. During the pressure-controlled ventilation, the gaseous inhalant is delivered to the patient with a suitable pressure that assists the lungs of the patient in inhaling the gaseous inhalant. During the volume-controlled ventilation, a suitable volume of the gaseous inhalant is delivered to the patient at regular time intervals to mimic (or imitate) the respiratory cycle. Mandatory breaths are always volume-controlled while spontaneous breaths may be pressure-controlled or volume-controlled. Operation of the ventilator 100 while providing the pressure-controlled ventilation and the volume-controlled ventilation is described later in the description.

The breathing system 102 may include suitable logic, circuitry, interfaces, and/or code, executable by the circuitry, that may be configured to facilitate delivery of the gaseous inhalant to the patient. The breathing system 102 may include a plurality of components including the bag valve 110 and the pressure line adaptor 112. The bag valve 110 may have a first opening and a second opening that allows the gaseous inhalant to flow through it. Compression of the bag valve 110 may cause the gaseous inhalant to flow to the pressure line adaptor 112. The pressure line adaptor 112 includes a front end that faces the bag valve 110 and a rear end that faces the patient. The gaseous inhalant enters the pressure line adaptor 112 via the front end. The pressure line adaptor 112 further includes a first pressure tap and a second pressure tap (shown in FIG. 2) positioned on either side of the orifice plate 114. The first pressure tap is positioned between the front end and the orifice plate 114, and the second pressure tap is positioned between the orifice plate 114 and the rear end. The pressure line adaptor 112 is configured to provide a channel to the gaseous inhalant to reach from the bag valve 110 to the patient. The first pressure tap is used by the control system 106 to determine an inflow pressure, i.e., a pressure due to flow of the gaseous inhalant between the front end of the pressure line adaptor 112 and an inflow face of the orifice plate 114. The second pressure tap of the pressure line adaptor 112 is used by the control system 106 to determine an outflow pressure, i.e., a pressure due to flow of the gaseous inhalant between an outflow face of the orifice plate 114 and the rear end of the pressure line adaptor 112. The inflow pressure sensor 132 is positioned at (or coupled to) the first pressure tap and the outflow pressure sensor 134 is positioned at (or coupled to) the second pressure tap. The inflow pressure sensor 132 is configured to record an inflow pressure due to the flow of the gaseous inhalant between the front end of the pressure line adaptor 112 and the orifice plate 114, and the outflow pressure sensor 134 is configured to record an outflow pressure due to the flow of the gaseous inhalant between the orifice plate 114 and the rear end of the pressure line adaptor 112. The plurality of components of the breathing system 102 and functioning thereof are described in detail in conjunction with FIG. 2.

The mechanical system 104 may include suitable logic, circuitry, interfaces, and/or code, executable by the circuitry, that may be configured to provide required compression to the bag valve 110. The mechanical system 104 may provide compressions to the bag valve 110 in synchronization to the breathing cycle (i.e., inhalation and exhalation) of the patient. The mechanical system 104 is configured to compress the bag valve 110 to synchronize with an inhalation period of the breathing cycle and release the bag valve 110 to synchronize with an exhalation period of the breathing cycle. The mechanical system 104 is further configured to provide such compressions to the bag valve 110 based on a compression value and a time-interval determined by the control system 106. The compression value refers to an amount by which the bag valve 110 has to be compressed. The motor driver 116 causes the motor 118 to operate in accordance with the compression value. In other words, the motor driver 116 provides an input to the motor 118 that causes the motor 118 to actuate the compression circuitry 120 to provide the bag valve 110 a compression that is proportional to the compression value.

The motor driver 116 may include suitable logic, circuitry, interfaces, and/or code, executable by the circuitry, that may be configured to facilitate operation of the motor 118. The motor driver 116 may be controlled by the control system 106 to regulate the compression of the bag valve 110 by the motor 118.

The motor 118 may include suitable logic, circuitry, interfaces, and/or code, executable by the circuitry, that when in operation, may be configured to actuate the compression circuitry 120 to compress the bag valve 110. In an example, the motor 118 may be a stepper motor or a brushless DC motor or a servo motor as long as a degree of rotation is controllable. The motor steps or the degrees by which the motor 118 rotates may be directly proportional to the compression value.

The compression circuitry 120 may include suitable logic, circuitry, interfaces, and/or code, executable by the circuitry that may be configured to physically push the bag valve 110 from at least one direction to perform compression of the bag valve 110. In an example, the compression circuitry 120 may include at least two plates positioned on opposite sides of the bag valve 110. In an instance, each of the two plates may be movable and may be moved from their respective home positions by the motor 118 to compress the bag valve 110. In another instance, one of the two plates may be fixed and the other plate may be moved from its home position by the motor 118 to compress the bag valve 110. A position of the compression circuitry 120, while compressing the bag valve 110 may be determined by the position sensor 124. In an embodiment, after the bag valve 110 is successfully compressed by the compression circuitry 120 in accordance with the compression value, the compression circuitry 120 is controlled by the motor 118 to attain the home position, thereby releasing the pressure on the bag valve 110. As a result, the bag valve 110 decompresses to attain its original shape.

The position sensor 124 may include suitable logic, circuitry, interfaces, and/or code, executable by the circuitry that may be configured to determine a current position of one or more components of the compression circuitry 120 while the bag valve 110 is being compressed or while the compression is being released from the bag valve 110. In an example, the position sensor 124 may be configured to determine current positions of the plates of the compression circuitry 120. The motor driver 116 may cause the motor 118 to stop or continue compressing the bag valve 110, via the compression circuitry 120, based on current positions of the plates. The bag valve 110 gets decompressed when the compression circuitry 120 moves away from the bag valve 110.

The temperature sensor 122 may include suitable logic, circuitry, interfaces, and/or code, executable by the circuitry that may be configured to determine temperature of the mechanical system 104. The control system 106 may monitor the temperature recorded by the temperature sensor 122 and may initiate an alarm based on the temperature of the mechanical system 104 being greater than or equal to a threshold temperature value.

The powering system 108 may include suitable logic, circuitry, interfaces, and/or code, executable by the circuitry that may be configured to power the mechanical system 104 and the control system 106. The powering system 108 may include an uninterrupted power supply (UPS) system, a supercapacitor, an inverter, a generator, a battery, a power source, or circuitry connected to a direct power supply, or the like. The powering system 108 may be coupled to the mechanical system 104 and the control system 106 via a wired medium.

The control system 106 may include suitable logic, circuitry, interfaces, and/or code, executable by the circuitry that may be configured to control the ventilator 100. The control system 106 is further configured to calibrate the ventilator 100 prior to its use for providing ventilation to the patient. Such calibration is performed by the control system 106 by correlating a plurality of compression values of the bag valve 110 and a plurality of values of a plurality of parameters with a volume of the gaseous inhalant that flows through the breathing system 102. The plurality of parameters may include a respiration rate (RR), an inhalation-exhalation (IE) ratio, a volume of the gaseous inhalant, and a positive end expiratory pressure (PEEP), desired for the patient. During calibration of the ventilator 100, the patient is assumed to be a pair of sample lungs or a volunteer. The RR refers to a count of breaths that the ventilator 100 is required to deliver to the user in a unit time. The IE ratio refers to a desired ratio of inspiratory time to expiratory time during the breathing cycle of the user. The desired volume of the gaseous inhalant to be delivered to the user refers to an amount of the gaseous inhalant that has to be delivered to the user during each inhalation period. The PEEP in the lungs of the user refers to a pressure to be maintained in the lungs of the user at end of the exhalation period. Maintenance of PEEP in the lungs prevents the lungs from collapsing due to passive exhalation. The plurality of parameters may further include a maximum inspiratory pressure for the user. Throughout the draft the terms "user" and "patient" are used interchangeably.

The HMI 126 may include suitable logic, circuitry, interfaces, and/or code, executable by the circuitry that may be configured to receive input settings for calibration and operation of the ventilator 100. The HMI 126 may include buttons, knobs, keypad, touch screen, or the like configured to be used to provide the input settings. The HMI 126 is described in detail in conjunction with FIG. 5.

The memory 128 may include suitable logic, circuitry, and interfaces that may be configured to store one or more instructions which when executed by one or more other components of the control system 106 cause the respective component to perform various operations for one or more operations of the ventilator 100. The memory 128 may be accessible by the processing circuitry 130. Examples of the memory 128 may include, but are not limited to, a random-access memory (RAM), a read only memory (ROM), a removable storage drive, a hard disk drive (HDD), a flash memory, a solid-state memory, or the like. It will be apparent to a person skilled in the art that the scope of the disclosure is not limited to realizing the memory 128 in the control system 106, as described herein. In another embodiment, the memory 128 may be realized in the form of a database working in conjunction with the control system 106, without departing from the scope of the disclosure.

The processing circuitry 130 may include suitable logic, circuitry, interfaces, and/or code, executable by the circuitry, that may be configured to execute instructions stored in the memory 128 to perform various operations for calibrating the ventilator 100 and controlling the ventilator 100 during implementation/operation (i.e., while providing ventilation). The processing circuitry 130 may be configured to perform various operations associated with data collection and data processing. The processing circuitry 130 may be implemented by one or more processors, such as, but not limited to, an application-specific integrated circuit (ASIC) processor, a reduced instruction set computing (RISC) processor, a complex instruction set computing (CISC) processor, and a field-programmable gate array (FPGA) processor. The one or more processors may also correspond to central processing units (CPUs), graphics processing units (GPUs), network processing units (NPUs), digital signal processors (DSPs), or the like. It will be apparent to a person of ordinary skill in the art that the processing circuitry 130 may be compatible with multiple operating systems.

In operation, during the calibration of the ventilator 100, a flow sensor is deployed, in the breathing system 102, to measure a volume of the gaseous inhalant being delivered to the patient as a result of the compression of the bag valve 110. The control system 106 is configured to receive first input settings for a plurality of values of the plurality of parameters via the HMI 126. The plurality of values may include a plurality of sets of calibration values for the plurality of parameters. Each set of calibration values may include a value corresponding to each parameter. For each set of calibration values, the processing circuitry 130 is configured to initiate an operation of the ventilator 100.

Based on the operation of the ventilator 100 for each set of calibration values, the processing circuitry 130 is configured to create a look-up table. For each set of calibration values, the processing circuitry 130 is configured to record a compression value of the bag valve 110 when the flow sensor records that the volume of gaseous inhalant flowing through the breathing system 102 is equal to the desired volume in the respective set of calibration values. The recorded compression values are included in the look-up table corresponding to the respective sets of calibration values. In an example, the processing circuitry 130 may record the compression values in terms of motor steps of the motor 118. For each set of calibration values, the processing circuitry 130 is further configured to measure a volume of the gaseous inhalant (hereinafter, referred to as "integral Q") flowing through the breathing system 102 based on the inflow pressure recorded by the inflow pressure sensor 132 and the outflow pressure recorded by the outflow pressure sensor 134. The processing circuitry 130 measures the integral Q corresponding to each set of calibration values when the flow sensor records that the volume of gaseous inhalant flowing through the breathing system 102 is equal to the desired volume of the gaseous inhalant in the respective set of calibration values. In other words, for each set of calibration values (i.e., a value of PEEP, a value of RR, a value of IE ratio, and a desired volume of the gaseous inhalant), the look-up table includes a corresponding compression value and a corresponding integral Q. The integral Q is a proxy or representation of the volume (Vf) of the gaseous inhalant. After successful calibration, the look-up table is stored in the memory 128. The volume of the gaseous inhalant is determined using equations (1) and (2) as mentioned below:

$$Q=K*\sqrt{E*(PG1(t)-PG2(t))} \quad (1)$$

$$\text{Integral } Q=\int Q(t)dt \quad (2)$$

where,

Integral Q may be determined using trapezoidal integral method, t refers to a time interval for corresponding breathing cycle and E is a factor used to extend a dynamic range of PG1−PG2, $PG1(t)=(P1-\text{Patmosphere})$, PG2(t)=(P2−Patmosphere), where Patmosphere is atmospheric pressure, P1 is inflow pressure, and P2 is outflow pressure, E is a multiple of 2, and $$K=\frac{f(RR, IE, PEEP)}{\sqrt{E}\sqrt{P_{atmosphere}}}.$$

The ventilator 100, upon calibration, is set for ventilating the patient. Although the flow sensor is used during the calibration of the ventilator 100, no flow sensor is used in the ventilator 100 during its operation post calibration. While ventilating the patient, the control system 106 is configured to control the breathing system 102 and the mechanical system 104 based on second input settings received by the control system 106 via the HMI 126. The control system 106 may be configured to receive the second input setting that may be indicative of a set of values for the plurality of parameters for a patient. The plurality of parameters for which the set of values is received may include a desired RR for the patient, a desired volume of the gaseous inhalant to be delivered to the patient, a desired IE ratio for the patient, and a desired PEEP to be maintained in the lungs of the patient.

While providing the volume-controlled ventilation, the processing circuitry 130 is configured to identify a compression value, from the look-up table, corresponding to the received set of values. In other words, the processing circuitry 130 identifies (or looks-up), in the look-up table, the RR, the volume of the gaseous inhalant, the IE ratio, and the PEEP, desired for the patient as per the received set of values and selects a compression value corresponding to the identified RR, the desired volume of the gaseous inhalant, the IE ratio, and the PEEP in the look-up table. The processing circuitry 130 is further configured to determine a time-interval during which the desired volume of the gaseous inhalant has to be delivered to the patient based on the set of values for the plurality of parameters. In an embodiment, the processing circuitry 130 may determine the time-interval based on values of the RR and IE ratio for the patient. The processing circuitry 130 may further identify (or looks-up), in the look-up table, the integral Q corresponding to the received set of values.

In an embodiment, an atmospheric pressure of a location where the ventilator 100 is deployed may be different from an atmospheric pressure of a location where the ventilator 100 was calibrated. In such a scenario, the processing circuitry 130 may be further configured to correct the identified integral Q with respect to the atmospheric pressure of the location where the ventilator 100 is deployed. The identified integral Q may be corrected using equation (3) as mentioned below:

$$\text{Integral } Q_{Deployement} = \text{Integral } Q_{Calibration} * \sqrt{\frac{P_{Deployment}}{P_{Calibration}}} \quad (3)$$

where, $P_{Deployment}$ is atmospheric pressure of a location where the ventilator 100 is deployed, and $P_{Calibration}$ is atmospheric pressure of a location where the ventilator 100 is calibrated.

The processing circuitry 130 is configured to cause the mechanical system 104 to compress the bag valve 110 based on the identified compression value and the determined time-interval. The processing circuitry 130 may communicate instructions to the motor driver 116 to actuate the motor 118 to cause the compression circuitry 120 to compress the bag valve 110 during the inhalation period. As a result, the mechanical system 104 compresses the bag valve 110 as per the compression value during the inhalation period resulting in the gaseous inhalant to flow into the lungs of the patient via the breathing system 102.

The processing circuitry 130 is further configured to determine an actual volume of the gaseous inhalant delivered to the patient due to the compression of the bag valve 110 during the time-interval. The processing circuitry 130 determines the actual volume of the gaseous inhalant delivered to the patient based on the inflow pressure recorded by the inflow pressure sensor 132 and the outflow pressure recorded by the outflow pressure sensor 134. For example, the processing circuitry 130 may measure integral Q based on the inflow pressure and the outflow pressure. Here, the measured integral Q corresponds to the actual volume of the gaseous inhalant delivered to the patient.

Further, the processing circuitry 130 is configured to determine a deviation between the actual volume of the gaseous inhalant and the desired volume of the gaseous inhalant. The deviation may be caused by a variety of factors including, but not limited to, compliance of the patient's lungs, leakages in the breathing system etc. The processing circuitry 130 may determine the deviation between the actual volume of the gaseous inhalant and the desired volume of the gaseous inhalant based on a difference between the measured integral Q and an integral Q corresponding to the desired volume of the gaseous inhalant in the look-up table. The processing circuitry 130 is further configured to modify the compression value of the bag valve 110 based on the determined deviation. In an instance, when the actual volume of the gaseous inhalant is determined to be less than the desired volume of the gaseous inhalant, the processing circuitry 130 may be configured to increase the compression value of the bag valve 110. In other words, the compression value is increased to match a measured integral Q with the integral Q corresponding to the desired volume of gaseous inhalant in the look-up table. In another instance, when the actual volume of the gaseous inhalant is greater than the desired volume of the gaseous inhalant, the processing circuitry 130 may be configured to decrease the compression value of the bag valve 110. In other words, the compression value is decreased to match the measured integral Q with the integral Q corresponding to the desired volume of gaseous inhalant in the look-up table. The processing circuitry 130 is configured to modify the compression value iteratively to match the actual volume of the gaseous inhalant with the desired volume of the gaseous inhalant. When the measured integral Q matches the integral Q corresponding to the desired volume of the gaseous inhalant in the look-up table, the processing circuitry 130 determines that the actual volume of the gaseous inhalant is equal to the desired volume of gaseous inhalant. Subsequently, the processing circuitry 130 continues to control a compression of the bag valve 110 in accordance with a compression value at which the actual volume of the gaseous inhalant matched (or became equal to) the desired volume of the gaseous inhalant. In other words, during the volume-controlled ventilation, the control system 106 iteratively controls a compression of the bag valve 110 across breathing cycles so as to deliver the desired volume of the gaseous inhalant to the patient during inhalation.

In an example, the measured integral Q exceeds the integral Q corresponding to the desired volume of the gaseous inhalant in the look-up table by "5 percent". In such an example, the compression value of the bag valve 110 may be decreased by "5 percent" to match the measured integral Q with the integral Q corresponding to the desired volume of the gaseous inhalant in the look-up table.

In another example, the integral Q corresponding to the desired volume of the gaseous inhalant in the look-up table exceeds the measured integral Q by "2 percent". In such an example, the compression value of the bag valve 110 may be increased by "2 percent" to match the measured integral Q with the integral Q corresponding to the desired volume of the gaseous inhalant in the look-up table.

In an embodiment, the processing circuitry 130 may detect that the patient is trying to breathe on their own and has taken a spontaneous breath. The spontaneous breath refers to a respiratory cycle initiated by respiratory muscles of the patient. In an instance, when the processing circuitry 130 detects the spontaneous breath, it supports the spontaneous breath by either delivering a set volume (volume-controlled) or a set pressure (pressure-controlled). The processing circuitry 130 reschedules a scheduled inhalation (or breath) after each spontaneous breath. In an example, the scheduled inhalation may get rescheduled after an exhalation period of the spontaneous breath. The processing circuitry 130 controls the mechanical system 104 and the breathing system 102 to provide the scheduled inhalation to the patient when no spontaneous breath is detected after the exhalation period. However, the processing circuitry 130 may again reschedule the scheduled inhalation (or breath) if another spontaneous breath is detected during the exhalation period. This process is also referred to as Breath Synchronization. Therefore, the patient is continuously provided with the gaseous inhalant in case he/she is not breathing on their own.

While providing the pressure-controlled ventilation, the plurality of parameters for which the set of values is received may include an inspiratory pressure required for the patient, the desired RR for the patient, the PEEP to be maintained in the lungs, a maximum inspiratory pressure for the patient, and a desired IE ratio for the patient. The control system 106 is configured to regulate, by way of the mechanical system 104, a flow of the gaseous inhalant to achieve the inspiratory pressure required by the patient. Once the required inspiratory pressure is achieved, the control system 106 is configured to regulate the flow of the gaseous inhalant to maintain required inspiratory pressure. The flow is regulated by decreasing/increasing corresponding compression value for compressing the bag valve 110. The required inspiratory pressure allows the gaseous inhalant to flow through the breathing system 102 and to the lungs of the patient while maintaining the required pressure. The gaseous inhalant while flowing with the required inspiratory pressure causes the air pipes and lungs of the patient to open and get filled with the gaseous inhalant. At the end of the inhalation period, an outflow of the gaseous inhalant from the breathing system 102 stops while maintaining PEEP in the lungs. During exhalation, an expiratory gas coming out of the lungs gets passively exhaled. A non-rebreathable valve (shown in FIG. 2) prevents the exhaled expiratory gas from getting mixed with the gaseous inhalant. In the pressure-controlled ventilation, the control system 106 is configured to iteratively control a compression of the bag valve 110 in one breath cycle (during inspiration and expiration) so as to achieve the inspiratory pressure required by the patient during inspiration and the PEEP during expiration. A current level of the inspiratory pressure maintained in the lungs of the patient may be determined using the outflow pressure recorded by the outflow pressure sensor 134.

In an embodiment, the processing circuitry 130 is configured to initiate an audio/visual alarm based on one of an unsuitable PEEP being maintained in the lungs, a change (increase/decrease) in compliance of the lungs, incompliant/unsuitable input settings received by the control system 106, a conflict in the input settings, interruption in the delivery of the gaseous inhalant, abnormal inflow/outflow pressure, or the like.

Figure 2:
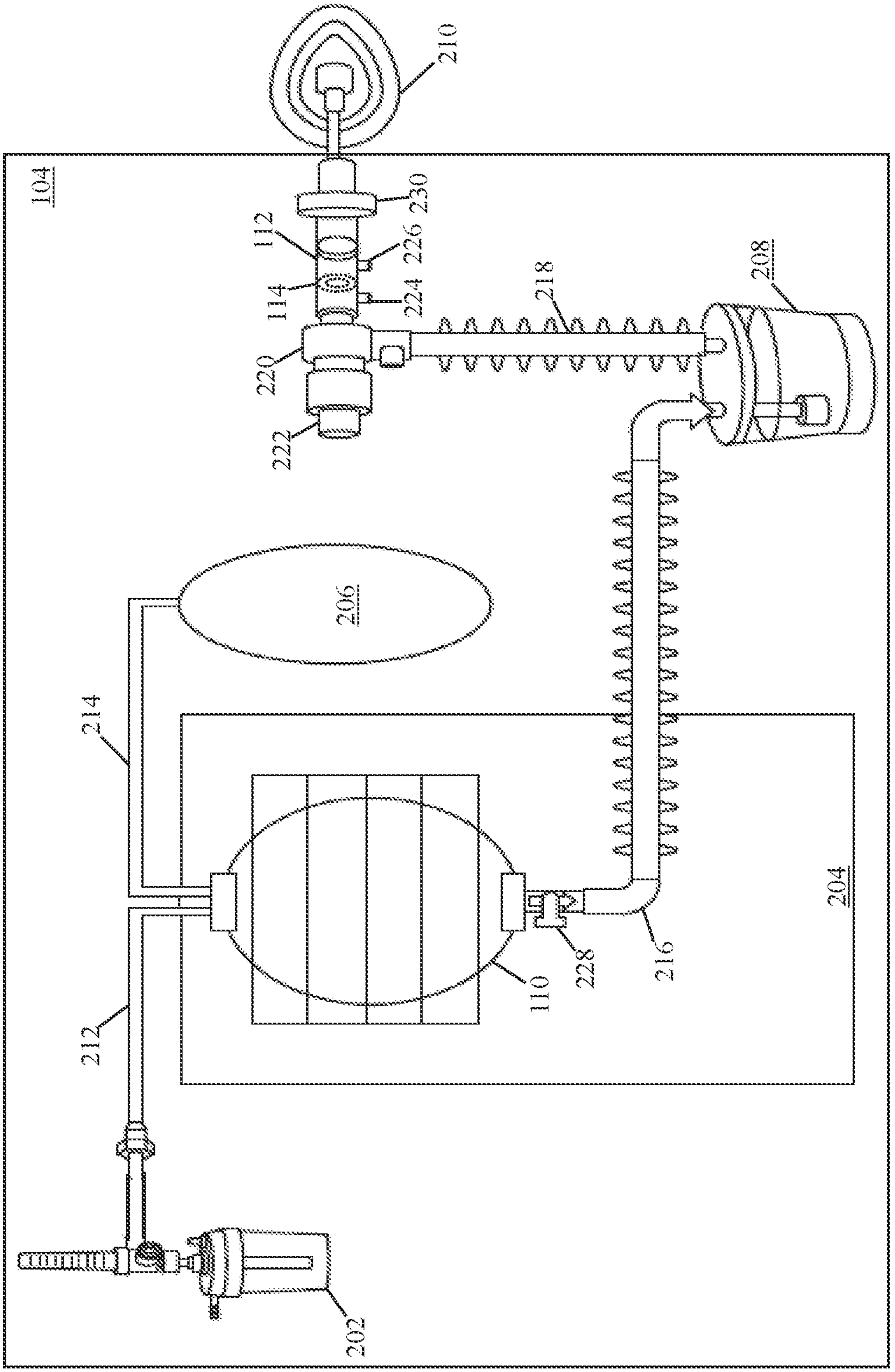
FIG. 2 is a block diagram that illustrates a breathing system of FIG. 1, in accordance with an exemplary embodiment of the disclosure.

FIG. 2 is a block diagram that illustrates the breathing system of FIG. 1, in accordance with an exemplary embodiment of the disclosure. Referring to FIG. 2, the breathing system 102 includes a gaseous inhalant source 202, a respirator 204 including the bag valve 110, a gaseous inhalant reservoir 206, a humidifier 208, and the pressure line adaptor 112 having the orifice plate 114. The breathing system 102 is further coupled to a patient interface 210.

The gaseous inhalant source 202 is coupled to the bag valve 110 via a first tubular assembly 212. The gaseous inhalant reservoir 206 is coupled to the bag valve 110 via a second tubular assembly 214. The bag valve 110 is coupled to the humidifier 208 via a third tubular assembly 216. The humidifier 208 is coupled to the non-rebreathable valve (hereinafter, referred to and designated as "non-rebreathable valve 220") via a fourth tubular assembly 218. The non-rebreathable valve 220 is coupled to a PEEP valve 222, and the pressure line adaptor 112. As shown, the pressure line adaptor 112 includes the orifice plate 114, the first pressure tap (hereinafter, the first pressure tap is referred to and designated as "the first pressure tap 224"), and the second pressure tap (hereinafter, the second pressure tap is referred to and designated as "the second pressure tap 226").

The gaseous inhalant source 202 may be configured to store the gaseous inhalant and supply the gaseous inhalant to the bag valve 110. The gaseous inhalant source 202 may be a cylinder, piped outlet, or the like. The gaseous inhalant source 202 may be refilled based on an availability of the gaseous inhalant therein.

The gaseous inhalant reservoir 206 may be configured to store the gaseous inhalant and supply the gaseous inhalant to the bag valve 110. The gaseous inhalant reservoir 206 may be an optional source of the gaseous inhalant that is coupled to the bag valve 110. The gaseous inhalant reservoir 206 is coupled to the bag valve 110 to achieve a maximum ventilation capacity of the ventilator 100.

The respirator 204 may include suitable components and structure that allows the flow of the gaseous inhalant through the breathing system 102. As shown, the respirator 204 includes the bag valve 110 that is compressed by the mechanical system 104 to initiate the flow of the gaseous inhalant through the breathing system 102 for delivering to the patient via the patient interface 210. The gaseous inhalant, based on the compression of the bag valve 110, flows to the humidifier 208 via the third tubular assembly 216. Further, pressure due to the flow of the gaseous inhalant is regulated by a pop-off valve 228. The pop-off valve 228 is an additional safety feature that ensures that excessive pressure is never applied to the patient's lungs.

The humidifier 208 may include suitable logic, circuitry, interfaces, and/or code, executable by the circuitry that heats the flowing gaseous inhalant to maintain an appropriate temperature of the gaseous inhalant. The humidifier 208 may include a liquid (such as water or any other liquid) and heating circuitry that is configured to heat the liquid. The gaseous inhalant passes through the warm liquid in the humidifier 208 that heats it up to a suitable temperature. The temperature of the liquid in the humidifier 208 may be controlled via the heating circuitry. The gaseous inhalant flowing out of the humidifier 208 flows to the pressure line adaptor 112 via the fourth tubular assembly 218 and the non-rebreathable valve 220.

The non-rebreathable valve 220 allows the gaseous inhalant to flow to the pressure line adaptor 112 and restricts exhaled gas from flowing back to the breathing system 102 or getting mixed with the gaseous inhalant.

The breathing system 102 further includes the PEEP valve 222. The PEEP valve 222 may include suitable logic, circuitry, and structure that may maintain the PEEP in the lungs of the patient. The PEEP valve 222 may have a plurality of pressure settings that may be selected by actuating the PEEP valve 222 to maintain specific PEEP in the lungs of the patient.

The orifice plate 114 is positioned between the first pressure tap 224 and the second pressure tap 226. The inflow pressure sensor 132 is positioned at (or coupled to) the first pressure tap 224 and the outflow pressure sensor 134 is positioned at (or coupled to) the second pressure tap 226. In other words, the inflow pressure sensor 132 and the outflow pressure sensor 134 are positioned on either side of the orifice plate 114. The orifice plate 114 restricts the flow of the gaseous inhalant due to its nozzle like structure. Such restriction increases inflow pressure and decreases the outflow pressure (in accordance with "Bernoulli's principle"). In other words, such restriction increases the pressure being caused due to flow of the gaseous inhalant between the front end of the pressure line adaptor 112 and the inflow face of the orifice plate 114 and decreases the pressure being caused due to flow of the gaseous inhalant between the outflow face of the orifice plate 114 and the rear end of the pressure line adaptor 112.

The breathing system 102 further includes heat and moisture exchanger (HME) filter 230. The HME filter 230 stores moisture from the exhaled expiratory gas. The moisture retains heat from inhaled gaseous inhalant. During inspiration, incoming gaseous inhalant collects this moisture and carries them as vapor into the lungs of the patient and maintains an appropriate temperature of the lungs. Further, the HME filter 230 is configured to filter particles present in the gaseous inhalant, thus also serving as an anti-microbial filter. The gaseous inhalant flowing out of the HME filter 230 is delivered to the patient via the patient interface 210.

The patient interface 210 may refer to an interface between the ventilator 100 and the patient. In an embodiment, the patient interface 210 may include a mask or tube having a proximal end associated with the breathing system 102 and a distal end facing the patient. The patient interface 210 may be configured to receive the gaseous inhalant from the breathing system 102 and deliver the gaseous inhalant to the patient. The proximal end of the patient interface 210 may be coupled to the breathing system 102 and the distal end of the patient interface 210 may be in communication with the air-way of the patient in an invasive or non-invasive manner.

In operation, the bag valve 110 receives the gaseous inhalant from the gaseous inhalant source 202 and the gaseous inhalant reservoir 206 via the first tubular assembly 212 and the second tubular assembly 214, respectively. Based on the compression of the bag valve 110 by the mechanical system 104, the gaseous inhalant flows via the third tubular assembly 216 to the humidifier 208. The gaseous inhalant gets warmed in the humidifier 208 and flows via the fourth tubular assembly 218 to the non-rebreathable valve 220. Further, the gaseous inhalant passes via the pressure line adaptor 112. The gaseous inhalant enters the pressure line adaptor 112 via the front end of the pressure line adaptor 112. Upon entering the pressure line adaptor 112, the inflow pressure is recorded by the inflow pressure sensor 132. Subsequently, the gaseous inhalant passes through the orifice plate 114. The outflow pressure is recorded by the outflow pressure sensor 134 when the gaseous inhalant flows through the outflow face of the orifice plate 114. Further, the gaseous inhalant flows through the HME filter 230 and one or more particles present in the gaseous inhalant get filtered. Subsequently, the gaseous inhalant gets delivered to the patient via the patient interface 210.

It will be apparent to a person skilled in the art that the breathing system 102 described herein is exemplary and does not limit the scope of the disclosure. In other embodiments, the breathing system 102 may include additional or different components and may operate in a different or similar manner to deliver the gaseous inhalant to the patient.

Figure 3A:
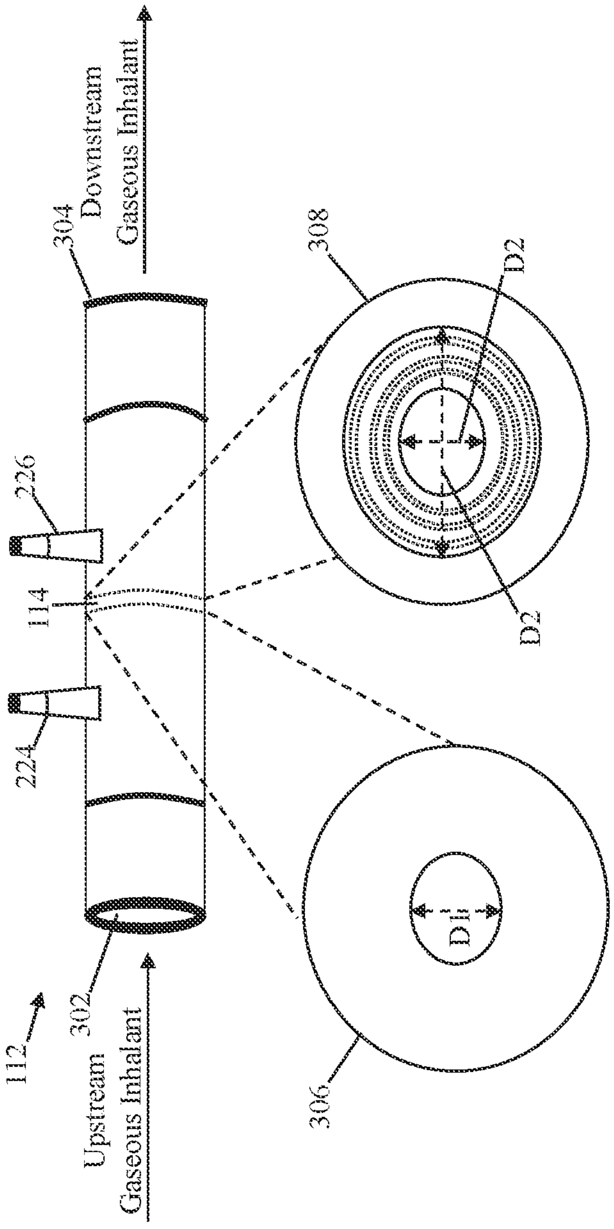
FIG. 3A is a schematic diagram that illustrates a pressure line adaptor used in the ventilator of FIG. 1, in accordance with an exemplary embodiment of the disclosure.

FIG. 3A is a schematic diagram that illustrates the pressure line adaptor used in the ventilator of FIG. 1, in accordance with an exemplary embodiment of the disclosure. Referring to FIG. 3A, shown is a front view of the pressure line adaptor 112. The pressure line adaptor 112 includes the front end (hereinafter, the front end is referred to and designated as "the front end 302") and the rear end (hereinafter, the rear end is referred to and designated as "the rear end 304"). As shown, the orifice plate 114 is positioned between the front end 302 and the rear end 304. The inflow face (hereinafter, the inflow face is referred to and designated as "the inflow face 306") of the orifice plate 114 faces the front end 302, and the outflow face (hereinafter, the outflow face is referred to and designated as "the outflow face 308") of the orifice plate 114 faces the rear end 304. The inflow face 306 allows an inflow of the gaseous inhalant via the orifice plate 114 and the outflow face 308 allows an outflow of the gaseous inhalant from the orifice plate 114.

Hereinafter, the first pressure tap 224 is referred to as "inflow pressure tap 224" and the second pressure tap 226 is referred to as "outflow pressure tap 226". As shown, the inflow pressure tap 224 is positioned between the front end 302 and the inflow face 306 and the outflow pressure tap 226 is positioned between the outflow face 308 and the rear end 304. The inflow pressure tap 224 allows for measurement of inflow pressure due to an upstream flow of the gaseous inhalant and the outflow pressure tap 226 allows for measurement of outflow pressure due to a downstream flow of the gaseous inhalant through the pressure line adaptor 112. In an embodiment, the orifice plate 114 is a quadrant radius orifice plate. The inflow face 306 is circular in shape and may have a diameter D1. Similarly, the outflow face 308 is also circular in shape and has a diameter D2, where D2 may be greater than D1.

Figure 3B:
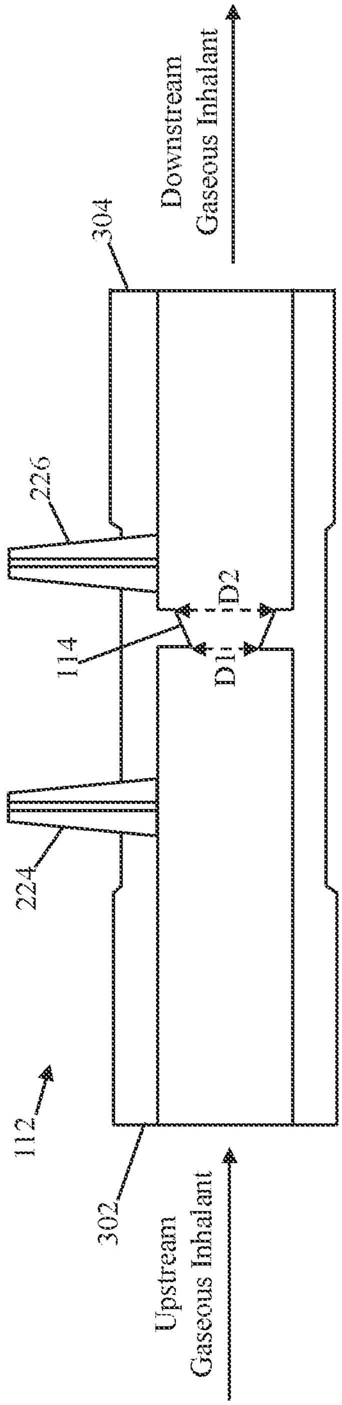
FIG. 3B is a schematic diagram that illustrates a longitudinal-sectional view of the pressure line adaptor of FIG. 3A, in accordance with an exemplary embodiment of the disclosure.

FIG. 3B is a schematic diagram that illustrates a longitudinal-sectional view of the pressure line adaptor of FIG. 3A, in accordance with an exemplary embodiment of the disclosure. As shown, the diameter D1 of the inflow face 306 of the orifice plate 114 is smaller than the diameter D2 of the outflow face 308 of the orifice plate 114. Therefore, the orifice plate 114 forms a nozzle like structure. The inflow face 306 of the orifice plate 114 (i.e., upstream) acts as a sharp edge orifice plate and the outflow face 308 of the orifice plate 114 is shaped like a flow nozzle. The inflow face 306 partially restricts the flow of the gaseous inhalant and the outflow face 308 allows for flow of an amount of the gaseous inhalant that passes through the inflow face 306.

Figure 3C:
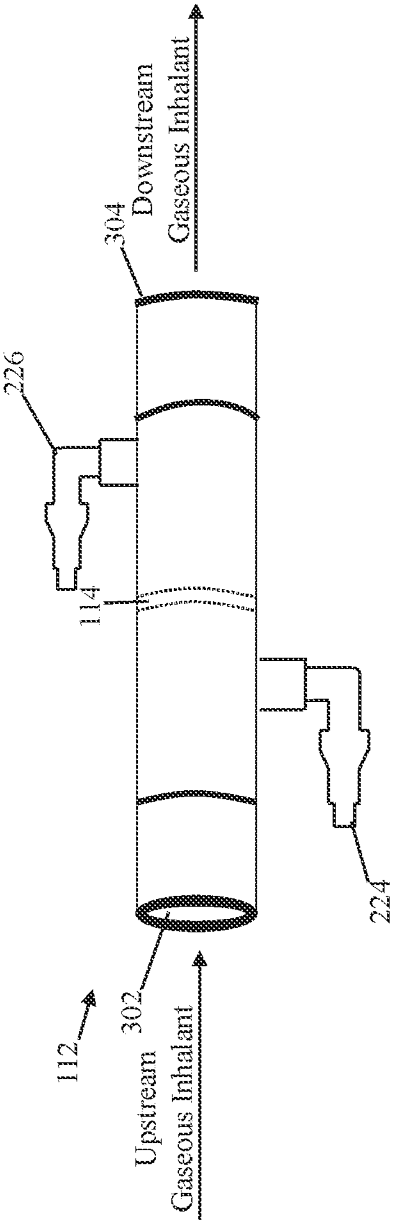
FIG. 3C is another schematic diagram that illustrates a pressure line adaptor, in accordance with another exemplary embodiment of the disclosure.

FIG. 3C is another schematic diagram that illustrates the pressure line adaptor, in accordance with another exemplary embodiment of the disclosure. Referring to FIG. 3C, illustrated is the pressure line adaptor 112 of a different embodiment. FIG. 3C is similar to FIG. 3A in all aspects except the structure of the inflow and outflow pressure taps 224 and 226. As shown in FIG. 3C, the inflow and outflow pressure taps 224 and 226 are "L-shaped" structures protruding out of a surface of the pressure line adaptor 112.

Figure 3D:
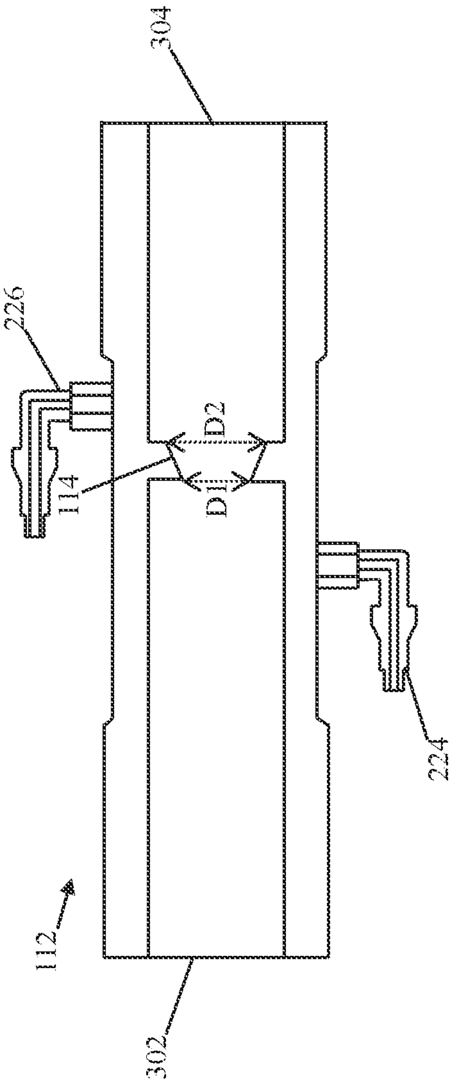
FIG. 3D is a schematic diagram that illustrates a longitudinal-sectional view of the pressure line adaptor of FIG. 3C, in accordance with another exemplary embodiment of the disclosure.

FIG. 3D is a schematic diagram that illustrates a longitudinal-sectional view of the pressure line adaptor of FIG. 3C, in accordance with another exemplary embodiment of the disclosure. Referring to FIG. 3D, the pressure line adaptor 112, as shown has the L-shaped inflow and outflow pressure taps 224 and 226 that are positioned on either side of the orifice plate 114. Further, the inflow and outflow pressure taps 224 and 226 may be color coded. Such color coding allows for easy identification of the inflow and outflow pressure taps 224 and 226. Therefore, operating the ventilator 100 in an uncontrolled and frantic environment gets swift and simple. In an example, the inflow pressure tap 224 may be color coded "RED" and the outflow pressure tap may be color coded "GREEN".

It will be apparent to a person skilled in the art that the pressure line adaptor 112 shown in FIGS. 3A, 3B, 3C, and 3D are exemplary and do not limit the scope of the disclosure. In other embodiments, the pressure line adaptor 112 may have a different structure and may include additional or different components.

FIG. 4 is a table that illustrates an exemplary look-up table, in accordance with an exemplary embodiment of the disclosure. Referring to FIG. 4, shown is the look-up table (hereinafter, the look-up table is referred to and designated as "the look-up table 400") generated by the control system 106. The look-up table 400 includes the plurality of values of the plurality of parameters that is received during a calibration of the ventilator 100. As shown, the plurality of parameters may include PEEP (in millimeterH2O), desired volume of the gaseous inhalant (Vt) (in milliliter), RR (in breaths per minute), IE ratio (inhalation time:exhalation time). For the sake of brevity, the look-up table 400 is shown to include five sets of calibration values (i.e., S1, S2, S3, S4, and S5) for the plurality of parameters. The look-up table 400 further includes a compression value and an integral Q corresponding to each set of calibration values. In other words, the look-up table 400 is generated by correlating the plurality of compression values of the bag valve 110 and the plurality of values of the plurality of parameters with a volume of the gaseous inhalant (i.e., integral Q) that flows through the breathing system 102. Determination of the compression values and the measurement of the integral Qs have been described in the foregoing description of FIG. 1.

Referring to the first set of calibration values S1, the PEEP to be maintained in the lungs is "30 millimeterH2O (mmH2O)" that is to say a positive end-expiratory pressure equivalent of 30 millimeters water is applied on the lungs to prevent passive exhalation from the lungs. The first set of calibration values S1, further includes the desired volume of the gaseous inhalant (Vt) to be delivered to the patient within the time-interval to be "250 milliliters (ml)". The first set of calibration values S1, further includes the RR to be "10 breaths per minute (bpm)" and the IE ratio to be "1:2". Therefore, the patient breathes 10 times in each minute, and each breath cycle lasts for 6 seconds. Hence, based on the corresponding IE ratio, the breathing cycle has 2 seconds of the inhalation period and 4 seconds of the exhalation period. The look-up table 400 further includes the compression value "444" (i.e., motor steps of the motor 118 used as a proxy for compression value) and the integral Q to be "43056". The time-interval is determined, by the control system 106, for each set of calibration values based on values of corresponding RR and IE. The compression value applied to the bag valve 110 within the time-interval is used by the control system 106 to determine a compression rate. The integral Q is measured (or determined) based on the inflow pressure and the outflow pressure recorded by the inflow pressure sensor 132 and the outflow pressure sensor 134, respectively, when the first set of calibration values S1 is inputted to the ventilator 100 via the HMI 126 (as described in foregoing description of FIG. 1). Similarly, the look-up table 400 includes the second through fifth sets of calibration values S2 through S5 and corresponding compression values and integral Qs.

In an example, the control system 106 may receive a set of values including PEEP "50 mmH2O", Vt "350 ml", RR "15 bpm", and IE "⅓". Subsequently, a compression value "556", corresponding to the fourth set of calibration values S4, is identified by the control system 106 from the look-up table 400. The control system 106 may further identify the desired volume of the gaseous inhalant that is to be delivered to the patient from the look-up table 400 corresponding to the fourth set of calibration values S4. In an embodiment, when an atmospheric pressure of a location where the ventilator 100 is deployed is different from an atmospheric pressure of a location where the ventilator 100 was calibrated, the control system 106 may correct the identified integral Q with respect to the atmospheric pressure of the location where the ventilator 100 is deployed (as described in the foregoing description of FIG. 1).

The control system 106 causes the mechanical system 104 to compress the bag valve 110 in accordance with the identified compression value 556 and a time-interval determined based on RR 15 bpm and IE ratio ⅓. Further, the control system 106 may measure an integral Q based on a current reading of the inflow pressure sensor 132 and the outflow pressure sensor 134 to be "55720". However, the measured integral Q "55720" may not match a value of integral Q corresponding to the fourth set of the calibration values S4. Hence, the integral Q is required to be reduced or increased by manipulating the inflow pressure and outflow pressure. Therefore, the control system 106 iteratively modifies the compression value of the bag valve 110 and measures corresponding integral Q. When the measured integral Q matches the integral Q corresponding to the fourth set of calibration values S4, the control system 106 determines that the actual volume of the gaseous inhalant is same as the identified desired volume of the gaseous inhalant.

In an embodiment, the look-up table 400 may include at least one of a proxy value for the compression value, an amount by which the bag valve 110 has to be compressed, a count of motor steps, or the like. In such an embodiment, the control system 106 may be aware of a correlation between the compression value and the amount by which the bag valve 110 has to be compressed.

It will be apparent to a person skilled in the art that the look-up table 400 illustrated herein is exemplary and does not limit the scope of the disclosure. In other embodiments, the look-up table 400 may include additional or different fields and corresponding values.

Figure 5:
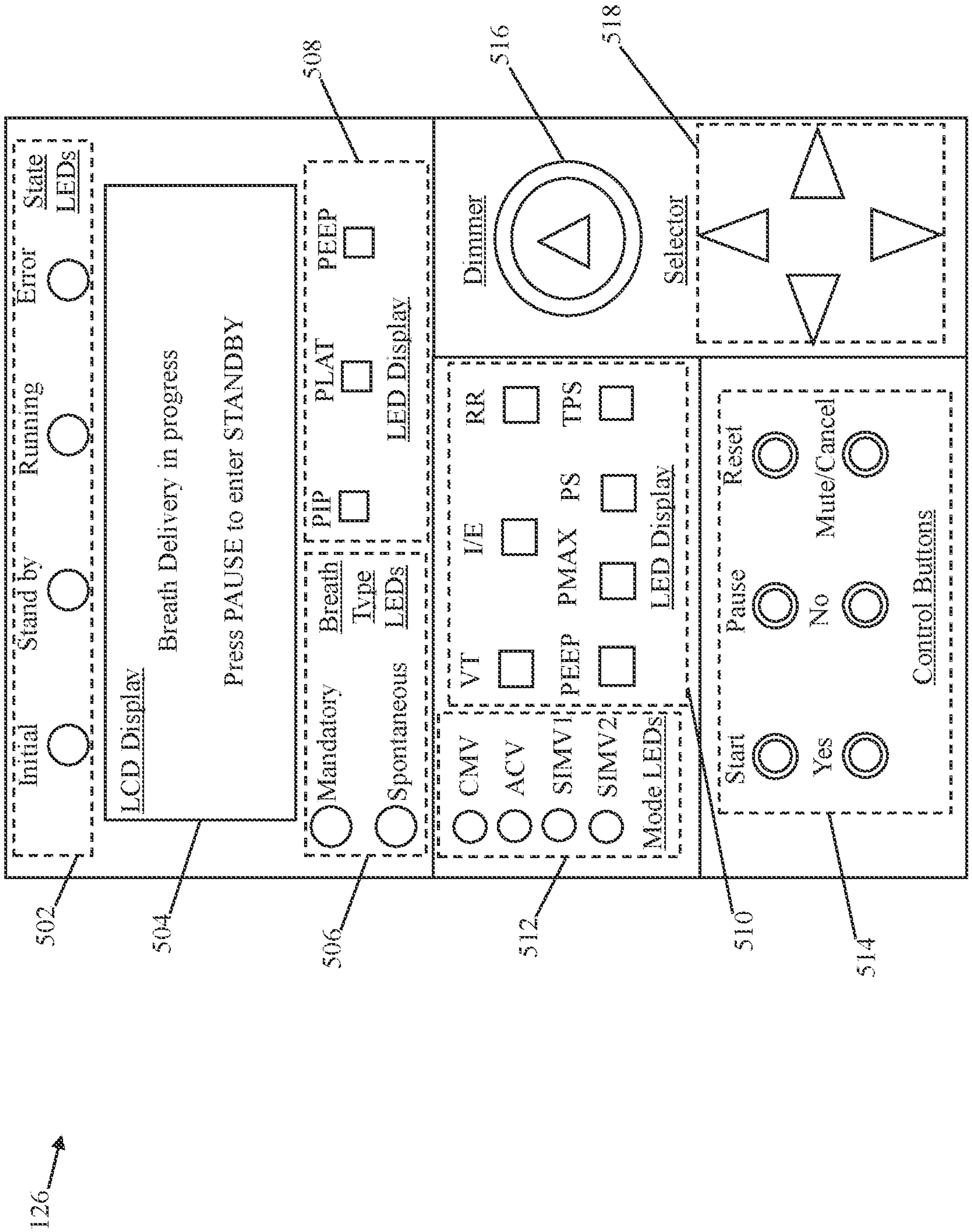
FIG. 5 is a schematic diagram that illustrates a human machine interface of a ventilator, in accordance with an exemplary embodiment of the disclosure.

FIG. 5 is a schematic diagram that illustrates an HMI for a ventilator, in accordance with an exemplary embodiment of the disclosure. Referring to FIG. 5, illustrated is the HMI 126 of the ventilator 100.

As shown, the HMI 126 includes four state light emitting diodes (LEDs) illustrated within a dashed rectangle 502. The state LEDs represent a plurality of operating states of the ventilator 100. The plurality of operating states may include an initial state ('Initial'), a stand-by state ('Stand by'), a running state ('Running'), and an error state ('Error'). The 'Initial' LED turns on when the ventilator 100 enters the initial state. The initial state is a first state that the ventilator 100 enters upon a power-on RESET or after a self-test. The initial state, when entered on power-on reset, initializes the control system 106 and performs self-tests of one or more components of the ventilator 100. The initial state, when entered after self-test, enables execution of pre-use checks that are to be performed before using the ventilator 100. The 'Stand By' LED turns on when the ventilator 100 enters the stand-by state. The stand-by state of the ventilator 100 prohibits delivery of the gaseous inhalant to the patient. One or more settings (such as the inputted set of values, a mode of ventilation, or the like) of the ventilator 100 may be modified while the ventilator 100 operates in the stand-by state. The 'Running' LED turns on when the ventilator 100 enters the running state. The running state of the ventilator 100 allows for delivery of the gaseous inhalant to the patient. The one or more settings of the ventilator 100 may also be modified while the ventilator 100 is in the running state. The modified settings may take effect from a subsequent breath being delivered to the patient. The 'Error' LED turns on when the ventilator 100 enters the error state. The error state of the ventilator 100 is enabled when an error is encountered while operating in any state of the ventilator 100. A corresponding error notification is displayed via a liquid crystal display (LCD) screen of the HMI 126. Further, the error may be indicated by blinking of a light emitting diode (LED) and/or sound of an audio alarm.

The HMI 126 may further include an LCD display 504. In an embodiment, the LCD display 504 may be touch-enabled may be used to receive one or more input settings. The LCD display 504 may present messages, prompts, or error messages. When the ventilator 100 operates in the running state, the LCD display 504 may present estimated lung compliance of the patient, a measured mandatory/spontaneous breaths per minute, the measured volume of the gaseous inhalant being delivered to the patient, or the like.

The HMI 126 may further include breath type LEDs, illustrated within a dashed rectangle 506, that are indicative of a type of breath being delivered to the patient. The type of breath may include the mandatory breath indicated by 'Mandatory' LED and the spontaneous breath indicated by 'Spontaneous' LED. The mandatory breath is a breath that is initiated and maintained by the ventilator 100 based on inputted set of values for the plurality of parameters. The 'Mandatory' LED turns on when the ventilator 100 provides mandatory breath to the patient. The spontaneous breath refers to movement of the gaseous inhalant in and out of the lungs in response to a movement in the respiratory muscles of the patient. The spontaneous breath is initiated by the patient on its own. The 'Spontaneous' LED turns on when spontaneous breath is detected for the patient.

The HMI 126 may further include LED displays corresponding to one or more parameters being measured while the ventilator 100 is operating in the running state. The one or more parameters are displayed via LED displays enclosed within the dashed rectangle 508. The one or more parameters may include peak inspiration pressure (PIP), plateau pressure (PLAT), and PEEP being maintained in the lungs. The PIP value is displayed via a 'PIP' LED, the PLAT value is displayed via a 'PLAT' LED, and the PEEP value is displayed via the 'PEEP' LED.

The HMI 126 may further include LED displays (enclosed within dashed rectangle 510) corresponding to the plurality of parameters. The LED displays 510 present values corresponding to each of the plurality of parameters. The LED displays 510 present values for the desired volume of the gaseous inhalant Vt, IE ratio, RR, and PEEP. The LED displays 510 further present values for maximum inspiration pressure (PMAX) for the lungs of the patient, support pressure (PS) for pressure supported ventilation, and auto mode or time of inspiration phase (TPS) for pressure supported ventilation. The Vt value is displayed via a 'VT' LED, the IE ratio is displayed via the 'IE Ratio' LED, the RR value is displayed via a 'RR' LED, and the PEEP value is displayed via the 'PEEP' LED. Further, the PMAX value is displayed via a 'PMAX' LED, the PS vale is displayed via the 'PS' LED, and the TPS value is displayed via the 'TPS' LED.

The HMI 126 may further include mode LEDs (enclosed within dashed rectangle 512) that indicate that the ventilator 100 is operating in one of plurality of modes of operation. As shown, the plurality of modes operation may include CMV, ACV, SIMV1, and SIMV2. The 'CMV' LED turns on when the CMV mode is activated for the ventilator 100 and the 'ACV' LED turns on when the ACV mode is activated for the ventilator 100. The 'SIMV1' LED turns on when the SIMV1 mode is activated for the ventilator 100 and the 'SIMV2' LED turns on when the SIMV2 mode is activated for the ventilator 100.

The HMI 126 further includes a plurality of control buttons (enclosed within a dashed rectangle 514) configured to control the ventilator 100. The plurality of control buttons may include a 'RESET' button, a 'PAUSE' button, a 'START' button, a 'CANCEL/MUTE' button, a 'YES' button, and a 'NO' button. The 'RESET' button may be configured to initiate a reset of the ventilator 100. Upon manipulation of the 'RESET' button, the ventilator 100 may transition to an initial state of operation. The 'PAUSE' button, when actuated while the ventilator 100 is in 'RUNNING' state, may be configured to cause the ventilator 100 to transition to the stand-by state, or a long press or double press may cause an inspiration pause in a subsequent breathing cycle of the patient. The 'START' button, when actuated while the ventilator 100 is in the stand-by state, may initiate delivery of the gaseous inhalant via the breathing system 102 based on the inputted set of values for the plurality of parameters. In an embodiment, when one or more settings of the ventilator 100 are changed while the ventilator 100 is in the running state, the 'START' button may act as a COMMIT button to confirm the one or more settings. The 'YES' button and the 'NO' button may be configured to receive, when actuated, an answer to one or more pre-use check questions while the ventilator 100 may operate in a TEST mode. In an embodiment, when one or more settings of the ventilator 100 are changed while the ventilator 100 is in the running state, the 'CANCEL/MUTE' button may be used to cancel the one or more settings. Further, the 'CANCEL/MUTE' button may be used to mute the audio of the ventilator 100.

The HMI 126 may further include a dimmer 516 that is a rotary knob that may be rotated to adjust a brightness level of the LED displays of the HMI 126. The HMI 126 may further include 'Selector' buttons (enclosed within dashed rectangle 518) that, when operated, may be configured to navigate a menu being presented via the HMI 126 and change input settings, or the like.

It will be apparent to a person skilled in the art that the HMI 126 illustrated herein is exemplary and does not limit the scope of the disclosure. In other embodiments, the HMI 126 may have a different architecture and may include additional or different components (for example, a radio button, a voice-enabled input interface, or the like) configured to receive the input settings.

Figure 6:
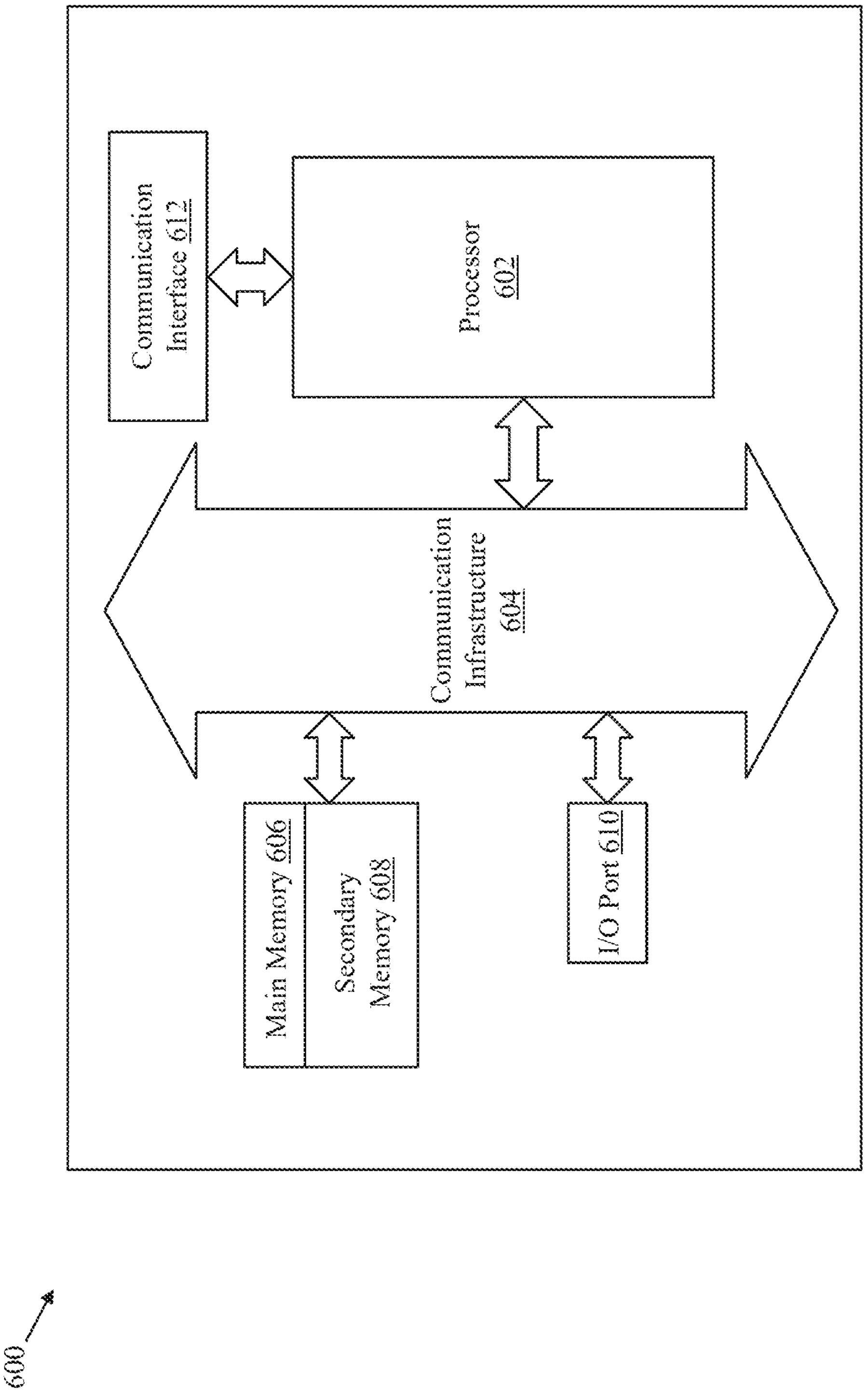
FIG. 6 is a block diagram that illustrates a system architecture of a computer system for controlling a ventilator, in accordance with an exemplary embodiment of the disclosure.

FIG. 6 is a block diagram that illustrates a system architecture of a computer system for controlling the ventilator, in accordance with an exemplary embodiment of the disclosure. An embodiment of the disclosure, or portions thereof, may be implemented as computer readable code on the computer system 600. In one example, the control system 106 of FIG. 1 may be implemented in the computer system 600 using hardware, software, firmware, non-transitory computer readable media having instructions stored thereon, or a combination thereof and may be implemented in one or more computer systems or other processing systems. Hardware, software, or any combination thereof may embody modules and components used to implement the methods of FIGS. 7, 8A, and 8B.

The computer system 600 may include a processor 602 that may be a special purpose or a general-purpose processing device. The processor 602 may be a single processor or multiple processors. The processor 602 may have one or more processor "cores." Further, the processor 602 may be coupled to a communication infrastructure 604, such as a bus, a bridge, a message queue, multi-core message-passing scheme, or the like. The computer system 600 may further include a main memory 606 and a secondary memory 608. Examples of the main memory 606 may include RAM, ROM, and the like. The secondary memory 608 may include a hard disk drive or a removable storage drive (not shown), such as a floppy disk drive, a magnetic tape drive, a compact disc, an optical disk drive, a flash memory, or the like. Further, the removable storage drive may read from and/or write to a removable storage device in a manner known in the art. In an embodiment, the removable storage unit may be a non-transitory computer readable recording media.

The computer system 600 may further include an input/output (I/O) port 610 and a communication interface 612. The I/O port 610 may include various input and output devices that are configured to communicate with the processor 602. Examples of the input devices may include a keyboard, a mouse, a joystick, a touchscreen, a microphone, and the like. Examples of the output devices may include a display screen, a speaker, headphones, and the like. The communication interface 612 may be configured to allow data to be transferred between the computer system 600 and various devices that are communicatively coupled to the computer system 600. Examples of the communication interface 612 may include a modem, a network interface, i.e., an Ethernet card, a communication port, and the like. Data transferred via the communication interface 612 may be signals, such as electronic, electromagnetic, optical, or other signals as will be apparent to a person skilled in the art. The signals may travel via a communications channel, such as the communication network, which may be configured to transmit the signals to the various devices that are communicatively coupled to the computer system 600. Examples of the communication channel may include a wired, and/or optical medium such as cable, fiber optics, and the like. The main memory 606 and the secondary memory 608 may refer to non-transitory computer readable mediums that may provide data that enables the computer system 600 to implement the methods illustrated in FIGS. 7, 8A, and 8B.

Figure 7:
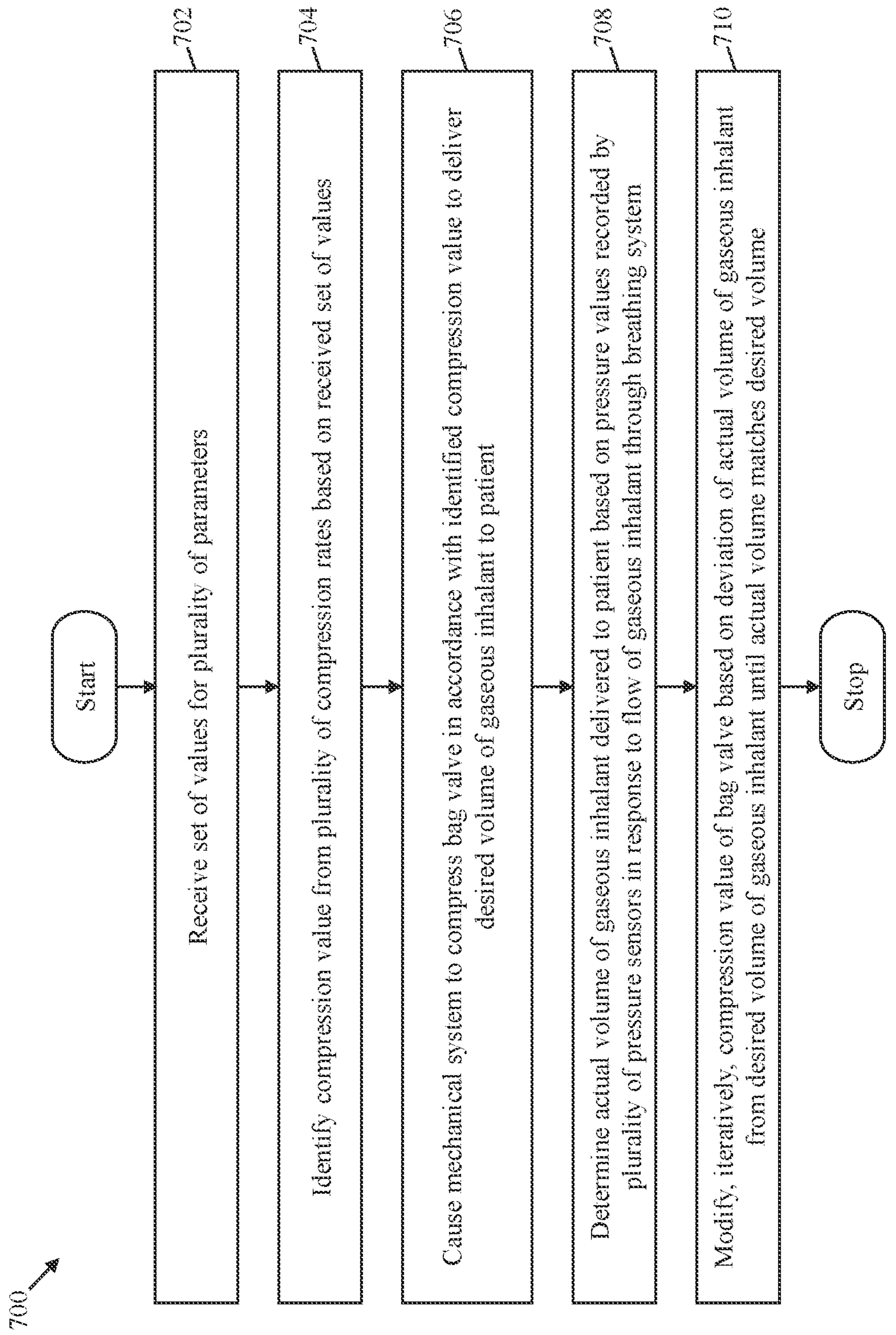
FIG. 7 is a flowchart that illustrates a method for controlling a ventilator, in accordance with an exemplary embodiment of the disclosure.

FIG. 7 is a flowchart that illustrates a method for controlling the ventilator, in accordance with an exemplary embodiment of the disclosure. Referring to FIG. 7, illustrated is the flowchart 700 of the method for controlling the ventilator 100.

At 702, the set of values for plurality of parameters is received. The control system 106 is configured to receive the set of values for the plurality of parameters. The plurality of parameters includes the respiration rate (RR), the inhalation-exhalation (IE) ratio, the desired volume of the gaseous inhalant, and the PEEP desired for the patient. The control system 106 is further configured to determine the time-interval (i.e., a compression time) during which the gaseous inhalant is to be delivered to the lungs of the patient.

At 704, the compression value is identified from the plurality of compression values in the look-up table 400 based on the received set of values. The control system 106 is configured to identify the compression value from the plurality of compression values in the look-up table 400 based on the received set of values.

At 706, the mechanical system 104 is caused to compress the bag valve 110 in accordance with the identified compression value and the determined time-interval (i.e., the compression time) to deliver the desired volume of gaseous inhalant to the patient. The control system 106 is configured to cause the mechanical system 104 to compress the bag valve 110 in accordance with the identified compression value to deliver the desired volume of the gaseous inhalant to the patient through the breathing system 102 within the determined time-interval. The compression of the bag valve 110 causes the gaseous inhalant to flow through the breathing system 102.

At 708, the actual volume of the gaseous inhalant delivered to the patient is determined based on the pressure values recorded by the plurality of pressure sensors (i.e., the inflow pressure sensor 132 and the outflow pressure sensor 134) in response to the flow of the gaseous inhalant through the breathing system 102. The control system 106 is configured to determine the actual volume of the gaseous inhalant delivered to the patient based on the pressure values (i.e., inflow pressure and outflow pressure) recorded by the plurality of pressure sensors in response to the flow of the gaseous inhalant through the breathing system 102.

At 710, the compression value of the bag valve 110 is iteratively modified based on the deviation of the actual volume of the gaseous inhalant from the desired volume of the gaseous inhalant until the actual volume matches the desired volume. The control system 106 is configured to iteratively modify the compression value of the bag valve 110 based on the deviation of the actual volume of the gaseous inhalant from the desired volume of the gaseous inhalant. The compression value is iteratively modified until the actual volume of the gaseous inhalant delivered to the patient matches the desired volume of the gaseous inhalant.

Figure 8A:
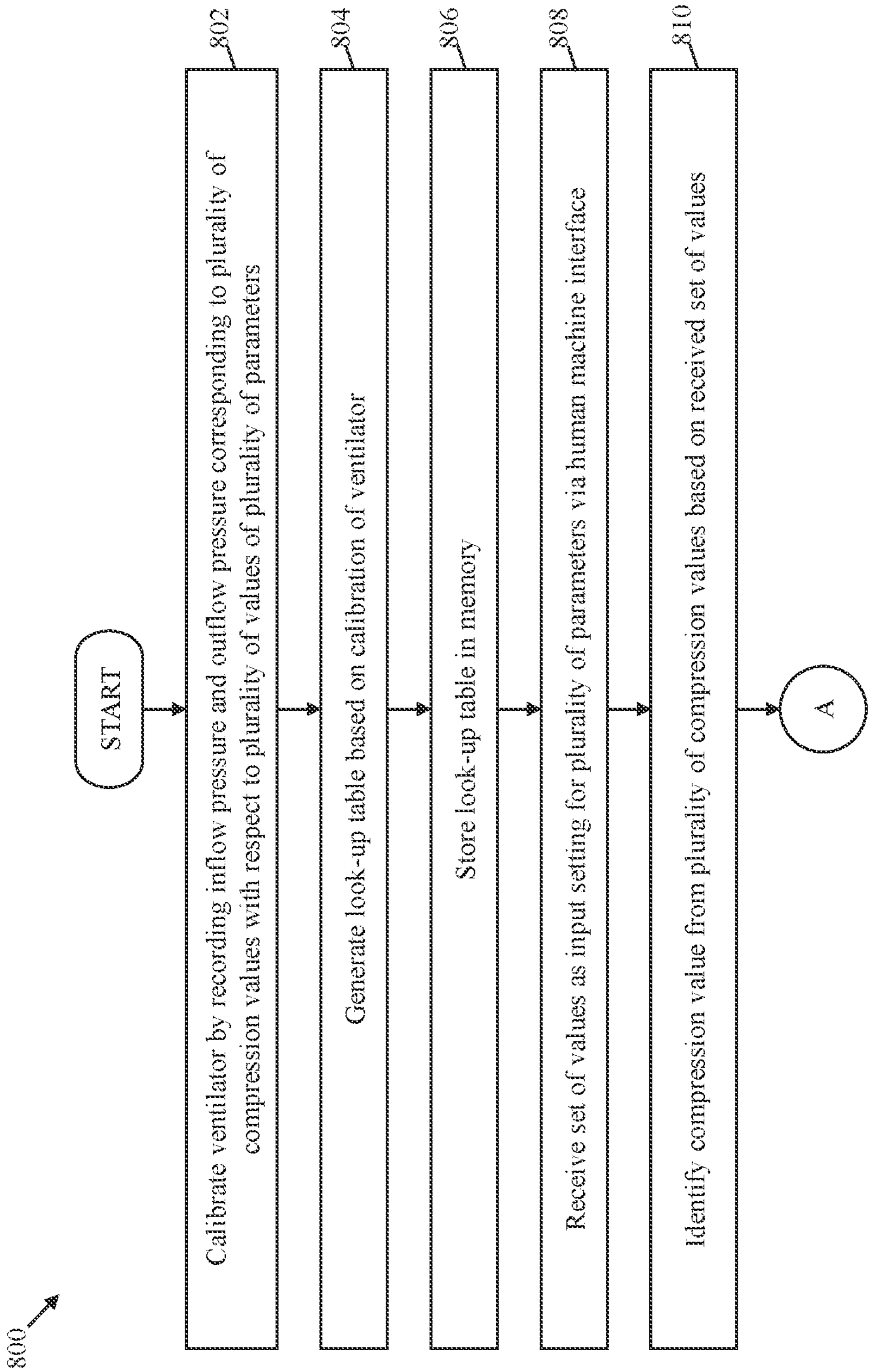
FIGS. 8A and 8B, collectively, illustrate a high-level flowchart of a method for controlling a ventilator, in accordance with an exemplary embodiment of the disclosure.
Figure 8B:
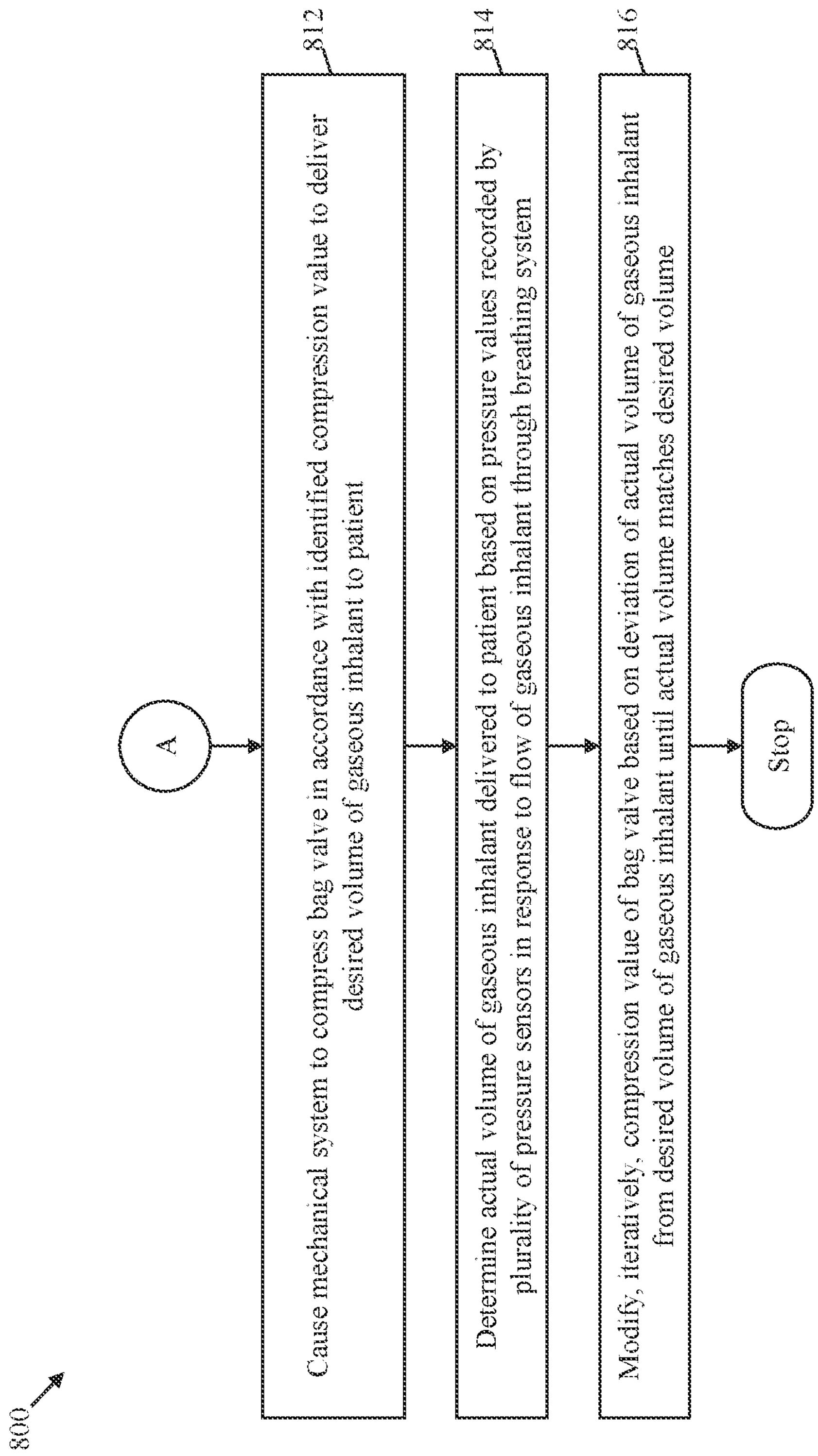

FIGS. 8A and 8B, collectively, illustrate a high-level flowchart of a method for controlling the ventilator, in accordance with an exemplary embodiment of the disclosure. Referring to FIG. 8A, illustrated is the high-level flowchart 800 for the method 800 for controlling the ventilator 100.

At 802, the ventilator 100 is calibrated by correlating the plurality of compression values and the plurality of values of the plurality of parameters with a volume (i.e., measured integral Q) of the gaseous inhalant that flows through the breathing system. The control system 106 is configured to calibrate the ventilator 100 by correlating the plurality of compression values of the bag valve 110 and the plurality of values of the plurality of parameters with the volume of the gaseous inhalant that flows through the breathing system 102.

At 804, the look-up table 400 is generated. The control system 106 is configured to generate the look-up table 400 during the calibration of the ventilator 100.

At 806, the look-up table 400 is stored in the memory 128. The control system 106 is configured to store the look-up table 400 that includes the plurality of compression values and the integral Qs corresponding to the plurality of values of the plurality of parameters in the memory 128.

At 808, the set of values is received as the second input setting for the plurality of parameters via the HMI 126. The control system 106 is configured to receive the set of values as the second input settings for the plurality of parameters via the HMI 126. In an embodiment, the control system 106 is further configured to determine the time-interval, within which the bag valve 110 is to be compressed in accordance with the identified compression value, based on the received set of values. The time-interval is determined based on values of the RR and the IE ratio.

At 810, the compression value from the plurality of compression values and the desired volume of the gaseous inhalant to be delivered to the patient is identified based on the received set of values. The control system 106 is configured to identify the compression value from the plurality of compression values in the look-up table 400 based on the received set of values. The control system 106 is further configured to determine the desired volume of the gaseous inhalant to be delivered to the patient from the look-up table 400 based on the received set of values.

At 812, the mechanical system 104 is caused to compress the bag valve 110 in accordance with the identified compression value to deliver the desired volume of gaseous inhalant to the patient within the determined time-interval. The control system 106 is configured to cause the mechanical system 104 to compress the bag valve 110 in accordance with the identified compression value to deliver the desired volume of the gaseous inhalant to the patient through the breathing system 102 within the time-interval. The compression of the bag valve 110 causes the gaseous inhalant to flow through the breathing system 102.

At 814, the actual volume of the gaseous inhalant delivered to the patient is determined based on the pressure values recorded by the plurality of pressure sensors (i.e., the inflow pressure sensor 132 and the outflow pressure sensor 134) in response to the flow of the gaseous inhalant through the breathing system 102. The control system 106 is configured to acquire the inflow pressure recorded by the inflow pressure sensor 132 and the outflow pressure recorded by the outflow pressure sensor 134. The control system 106 is configured to determine the actual volume of the gaseous inhalant delivered to the patient based on the inflow pressure and outflow pressure recorded by the plurality of pressure sensors in response to the flow of the gaseous inhalant through the breathing system 102. In other words, the control system 106 measures the integral Q representing the actual volume of the gaseous inhalant delivered to the patient based on the inflow pressure recorded by the inflow pressure sensor 132 and the outflow pressure recorded by the outflow pressure sensor 134 in response to the flow of the gaseous inhalant through the breathing system 102.

At 816, the compression value of the bag valve 110 is iteratively modified based on the deviation of the actual volume of the gaseous inhalant from the desired volume of the gaseous inhalant until the actual volume matches the desired volume. The control system 106 is configured to iteratively modify the compression value of the bag valve 110 based on the deviation of the actual volume of the gaseous inhalant from the desired volume of the gaseous inhalant. The compression value is iteratively modified until the actual volume of the gaseous inhalant delivered to the patient matches the desired volume of the gaseous inhalant.

Various embodiments of the disclosure provide the control system 106 for controlling the ventilator 100. The control system 106 may include the plurality of pressure sensors (for example, the inflow pressure sensor 132 and the outflow pressure sensor 134), the memory 128 configured to store the look-up table 400, and the processing circuitry 130. The control system 106 is configured to receive the set of values for the plurality of parameters and identify the compression value from the plurality of compression values in the look-up table 400 based on the received set of values. The control system 106 is further configured to cause the mechanical system 104 to compress the bag valve 110 of the breathing system 102 in accordance with the identified compression value to deliver the desired volume of the gaseous inhalant to the patient through the breathing system 102 within the time-interval. The compression of the bag valve 110 causes the gaseous inhalant to flow through the breathing system 102. The control system 106 is further configured to determine the actual volume of the gaseous inhalant delivered to the patient based on pressure values recorded by the plurality of pressure sensors (i.e., the inflow pressure sensor 132 and the outflow pressure sensor 134) in response to the flow of the gaseous inhalant through the breathing system 102. The control system 106 is further configured to iteratively modify the compression value of the bag valve 110 based on the deviation of the actual volume of gaseous inhalant from the desired volume of the gaseous inhalant. The compression value is iteratively modified until the actual volume of the gaseous inhalant delivered to the patient matches the desired volume of the gaseous inhalant.

Various embodiments of the disclosure provide a non-transitory computer readable medium having stored thereon, computer executable instructions, which when executed by a computer, cause the computer to execute one or more operations for controlling the ventilator 100. The one or more operations include receiving, by the control system 106 of the ventilator 100, the set of values for the plurality of parameters. The one or more operations further include identifying, by the control system 106, from the plurality of compression values included in the look-up table 400 of the ventilator 100, the compression value based on the received set of values. The look-up table 400 includes the plurality of compression values corresponding to the plurality of values of the plurality of parameters. The one or more operations further include causing, by the control system 106, the mechanical system 104 of the ventilator 100 to compress the bag valve 110 of the breathing system 102 of the ventilator 100 in accordance with the identified compression value to deliver the desired volume of the gaseous inhalant to the patient through the breathing system 102. The compression of the bag valve 110 causes the gaseous inhalant to flow through the breathing system 102 within the time-interval. The one or more operations further include determining the actual volume of the gaseous inhalant delivered to the patient based on the pressure values recorded by the plurality of pressure sensors (i.e., the inflow pressure sensor 132 and the outflow pressure sensor 134) of the ventilator 100 in response to the flow of the gaseous inhalant through the breathing system 102. The one or more operations further include modifying, iteratively, the compression value of the bag valve 110 based on the deviation of the actual volume of the gaseous inhalant from the desired volume of the gaseous inhalant. The compression value is iteratively modified until the actual volume of the gaseous inhalant delivered to the patient matches the desired volume of the gaseous inhalant.

The disclosed embodiments encompass numerous advantages. Exemplary advantages of the disclosed ventilator, systems, and methods include, but are not limited to, providing a cost-efficient and seamless ventilator and a control system for controlling an operation of the ventilator 100. The ventilator 100 allows for determining a volume of the gaseous inhalant being delivered to the ventilator 100 without using expensive flow sensors. Further, the control system 106 allows for a centralized approach for controlling the ventilator 100. The control system 106 requires minimum training for controlling one or more operations of the ventilator 100. Further, the look-up table 400 and instructions required for operations of the ventilator 100 require significantly less storage capacity and processing capability. Therefore, the control system 106 may be implemented with one or more basic software and hardware components. Further, the systems and methods disclosed herein may operate in an uncontrolled environment and hence are robust. The ventilator 100 disclosed herein is modular, compact, lightweight, and small in size. Therefore, the ventilator 100 may be easily moved from one place to another. Also, the modular and small size of the ventilator 100 allows for use of such ventilators in ambulances and as a result increases accessibility of ventilation facility. The ventilator 100 disclosed herein is low cost and hence may be manufactured in bulk within a budget. Therefore, an issue of insufficiency of ventilators in the healthcare sector may be significantly overcome. Also, easy availability of the ventilation facility may ensure life support to patients and may also prevent loss of lives due to lack of ventilators.

A person of ordinary skill in the art will appreciate that embodiments and exemplary scenarios of the disclosed subject matter may be practiced with various computer system configurations, including multi-core multiprocessor systems, minicomputers, mainframe computers, computers linked or clustered with distributed functions, as well as pervasive or miniature computers that may be embedded into virtually any device. Further, the operations may be described as a sequential process, however some of the operations may in fact be performed in parallel, concurrently, and/or in a distributed environment, and with program code stored locally or remotely for access by single or multiprocessor machines. In addition, in some embodiments, the order of operations may be rearranged without departing from the spirit of the disclosed subject matter.

Techniques consistent with the disclosure provide, among other features, ventilators, systems and methods for controlling ventilators. While various exemplary embodiments of the disclosed systems and methods have been described above, it should be understood that they have been presented for purposes of example only, and not limitations. It is not exhaustive and does not limit the disclosure to the precise form disclosed. Modifications and variations are possible in light of the above teachings or may be acquired from practicing of the disclosure, without departing from the breadth or scope.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

What is claimed is:

1. A ventilator, comprising:

a breathing system comprising a bag valve;

a mechanical system coupled to the breathing system and configured to compress the bag valve; and a control system coupled to the breathing system and the mechanical system, and comprising:

a plurality of pressure sensors configured to record pressure values based on flow of a gaseous inhalant through the breathing system;

a memory configured to store a look-up table, wherein the look-up table includes;

a plurality of compression values corresponding to a plurality of values of a plurality of parameters, and a plurality of first integral Qs corresponding to the plurality of values; and processing circuitry configured to:

receive a set of values for the plurality of parameters;

identify a compression value from the plurality of compression values in the look-up table based on the received set of values;

cause the mechanical system to compress the bag valve in accordance with the identified compression value to deliver a desired volume of the gaseous inhalant to a patient through the breathing system within a time-interval, wherein the compression of the bag valve causes the gaseous inhalant to flow through the breathing system;

determine a second integral Q, corresponding to an actual volume of the gaseous inhalant delivered to the patient, based on the pressure values recorded by the plurality of pressure sensors;

determine a deviation of the actual volume of the gaseous inhalant from the desired volume of the gaseous inhalant based on:

a first integral Q, of the plurality of first integral Qs, corresponding to the desired volume of the gaseous inhalant, and the determined second integral Q; and iteratively modify the compression value of the bag valve based on the determined deviation, wherein the compression value is iteratively modified until the actual volume of the gaseous inhalant delivered to the patient matches the desired volume of the gaseous inhalant.

2. The ventilator of claim 1, wherein the plurality of parameters includes a respiration rate (RR) for a user, an inhalation-exhalation (IE) ratio for the user, the desired volume of the gaseous inhalant to be delivered to the user, and a desired positive end expiratory pressure (PEEP) to be maintained in lungs of the user.

3. The ventilator of claim 1, wherein the breathing system further comprises a pressure line adaptor having a front end that faces the bag valve, and a rear end that faces the patient.

4. The ventilator of claim 3, wherein the pressure line adaptor comprises an orifice plate having an inflow face and an outflow face, the inflow face of the orifice plate allows an inflow of the gaseous inhalant via the orifice plate, and the outflow face of the orifice plate allows an outflow of the gaseous inhalant from the orifice plate.

5. The ventilator of claim 4, wherein the pressure line adaptor further comprises a first pressure tap and a second pressure tap, and wherein the first pressure tap is positioned between the front end of the pressure line adaptor and the orifice plate, and the second pressure tap is positioned between the orifice plate and the rear end of the pressure line adaptor.

6. The ventilator of claim 5, wherein the plurality of pressure sensors includes an inflow pressure sensor and an outflow pressure sensor, the inflow pressure sensor is positioned at the first pressure tap, and the outflow pressure sensor is positioned at the second pressure tap.

7. The ventilator of claim 6, wherein the inflow pressure sensor is configured to record an inflow pressure due to the flow of the gaseous inhalant between the front end of the pressure line adaptor and the orifice plate, and the outflow pressure sensor is configured to record an outflow pressure due to the flow of the gaseous inhalant between the orifice plate and the rear end of the pressure line adaptor.

8. The ventilator of claim 1, wherein the control system further comprises a human machine interface configured to receive the set of values as an input setting for the plurality of parameters.

9. The ventilator of claim 1, wherein the look-up table is generated during calibration of the ventilator, and wherein the ventilator is calibrated by correlation of the plurality of compression values of the bag valve and the plurality of values of the plurality of parameters with a volume of the gaseous inhalant that flows through the breathing system.

10. The ventilator of claim 1, wherein the processing circuitry is further configured to determine, based on the received set of values, the time-interval within which the bag valve is to be compressed in accordance with the identified compression value.

11. The ventilator of claim 1, wherein the processing circuitry is further configured to identify the desired volume of the gaseous inhalant, to be delivered to the patient, from the look-up table based on the received set of values.

12. The ventilator of claim 1, wherein the plurality of values includes a plurality of sets of calibration values for the plurality of parameters, and each first integral Q of the plurality of first integral Qs represents a volume of the gaseous inhalant that flows through the breathing system for a respective set of calibration values of the plurality of sets of calibration values.

13. The ventilator of claim 1, wherein the determination of the second integral Q, corresponding to the actual volume of the gaseous inhalant delivered to the patient, is independent of a flow sensor.

14. A control system comprising:

a plurality of pressure sensors configured to record pressure values based on flow of a gaseous inhalant through a breathing system of a ventilator, wherein the control system is configured to control the ventilator, and wherein the ventilator includes a mechanical system and the breathing system;

a memory configured to store a look-up table that includes:

a plurality of compression values corresponding to a plurality of values of a plurality of parameters, and a plurality of first integral Qs corresponding to the plurality of values; and processing circuitry configured to:

receive a set of values for the plurality of parameters;

identify a compression value from the plurality of compression values in the look-up table based on the received set of values;

cause the mechanical system to compress a bag valve of the breathing system in accordance with the identified compression value to deliver a desired volume of the gaseous inhalant to a patient through the breathing system within a time-interval, wherein the compression of the bag valve causes the gaseous inhalant to flow through the breathing system;

determine a second integral Q, corresponding to an actual volume of the gaseous inhalant delivered to the patient, based on the pressure values recorded by the plurality of pressure sensors;

determine a deviation of the actual volume of the gaseous inhalant from the desired volume of the gaseous inhalant based on:

a first integral Q, of the plurality of first integral Qs, corresponding to the desired volume of the gaseous inhalant, and the determined second integral Q; and iteratively modify the compression value of the bag valve based on the determined deviation, wherein the compression value of the bag valve is iteratively modified until the actual volume of the gaseous inhalant delivered to the patient matches the desired volume of the gaseous inhalant.

15. The control system of claim 14, wherein the plurality of parameters includes a respiration rate (RR) for a user, an inhalation-exhalation (IE) ratio for the user, the desired volume of the gaseous inhalant to be delivered to the user, a positive end expiratory pressure (PEEP) to be maintained in lungs of the user.

16. The control system of claim 14, wherein the processing circuitry is further configured to determine, based on the received set of values, the time-interval within which the bag valve is to be compressed in accordance with the identified compression value.

17. The control system of claim 14, wherein the processing circuitry is further configured to determine the desired volume of the gaseous inhalant, to be delivered to the patient, from the look-up table based on the received set of values.

18. A method of controlling a ventilator, the method comprising:

receiving, by a control system of the ventilator, a set of values for a plurality of parameters;

identifying, by the control system, from a plurality of compression values included in a look-up table of the ventilator, a compression value based on the received set of values, wherein the look-up table includes:

the plurality of compression values corresponding to a plurality of values of the plurality of parameters, and a plurality of first integral Qs corresponding to the plurality of values;

causing, by the control system, a mechanical system of the ventilator to compress a bag valve of a breathing system of the ventilator in accordance with the identified compression value to deliver a desired volume of a gaseous inhalant to a patient through the breathing system within a time-interval, wherein the compression of the bag valve causes the gaseous inhalant to flow through the breathing system;

determining a second integral Q, corresponding to an actual volume of the gaseous inhalant delivered to the patient, based on pressure values recorded by a plurality of pressure sensors of the ventilator, wherein the pressure values are recorded by the plurality of pressure sensors based on the flow of the gaseous inhalant through the breathing system;

determining a deviation of the actual volume of the gaseous inhalant from the desired volume of the gaseous inhalant based on:

a first integral Q, of the plurality of first integral Qs, corresponding to the desired volume of the gaseous inhalant, and the determined second integral Q; and modifying, iteratively, the compression value of the bag valve based on the determined deviation, wherein the compression value of the bag valve is iteratively modified until the actual volume of the gaseous inhalant delivered to the patient matches the desired volume of the gaseous inhalant.

19. The method of claim 18, wherein the plurality of parameters includes a respiration rate (RR) for a user, an inhalation-exhalation (IE) ratio for the user, the desired volume of the gaseous inhalant to be delivered to the user, and a positive end expiratory pressure (PEEP) to be maintained in lungs of the user.

20. The method of claim 18, further comprising recording, by the plurality of pressure sensors, an inflow pressure due to an inflow of the gaseous inhalant through an orifice plate of the breathing system, and an outflow pressure due to an outflow of the gaseous inhalant through the orifice plate.

* * * * *